United States Patent
Fischer et al.

(10) Patent No.: US 9,534,013 B2
(45) Date of Patent: Jan. 3, 2017

(54) PURIFICATION OF PROTEINS WITH CATIONIC SURFACTANT

(75) Inventors: Meir Fischer, Netanya (IL); Eliyahu Harosh, Ashdod (IL)

(73) Assignee: Horizon Pharma Rheumatology LLC, Lake Forest, IL (US)

( * ) Notice: Subject to any disclaimer, the term of this patent is extended or adjusted under 35 U.S.C. 154(b) by 516 days.

(21) Appl. No.: 11/918,292

(22) PCT Filed: Apr. 12, 2006

(86) PCT No.: PCT/US2006/013751
§ 371 (c)(1),
(2), (4) Date: Aug. 14, 2009

(87) PCT Pub. No.: WO2008/051178
PCT Pub. Date: May 2, 2008

(65) Prior Publication Data
US 2009/0317889 A1    Dec. 24, 2009

(51) Int. Cl.
*C07K 1/30* (2006.01)
(52) U.S. Cl.
CPC ........................................ *C07K 1/30* (2013.01)
(58) Field of Classification Search
CPC .......................................................... C07K 1/30
See application file for complete search history.

(56) References Cited

U.S. PATENT DOCUMENTS

| | | | |
|---|---|---|---|
| 3,451,996 A | 6/1969 | Sumyk et al. | |
| 3,616,231 A | 10/1971 | Bergmeyer et al. | |
| 3,931,399 A | 1/1976 | Bohn et al. | |
| 4,027,676 A | 6/1977 | Mattei | |
| 4,064,010 A | 12/1977 | Harris | |
| 4,141,973 A | 2/1979 | Balazs | |
| 4,169,764 A | 10/1979 | Takezawa et al. | |
| 4,179,337 A | 12/1979 | Davis et al. | |
| 4,297,344 A | 10/1981 | Schwinn et al. | |
| 4,301,153 A | 11/1981 | Rosenberg | |
| 4,312,979 A | 1/1982 | Takemoto et al. | |
| 4,315,852 A | 2/1982 | Leibowitz et al. | |
| 4,317,878 A | 3/1982 | Nakanishi et al. | |
| 4,343,735 A | 8/1982 | Menge et al. | |

(Continued)

FOREIGN PATENT DOCUMENTS

CN   1322243 A   11/2001
DE   837379      7/1976

(Continued)

OTHER PUBLICATIONS

Tomohiro, JP 2005-241424 (Sep. 8, 2005) (English language mechanical translation provided.*

(Continued)

*Primary Examiner* — Cherie M Stanfield

(74) *Attorney, Agent, or Firm* — Lando & Anastasi, LLP

(57) ABSTRACT

The subject invention provides a method for purifying a target protein from a mixture comprising the target protein and contaminating protein, comprising the steps of exposing the mixture to an effective amount of a cationic surfactant such that the contaminating protein is preferentially precipitated and recovering the target protein. Proteins purified according to the method of the invention are also provided.

30 Claims, 7 Drawing Sheets

(56) References Cited

U.S. PATENT DOCUMENTS

| | | | |
|---|---|---|---|
| 4,343,736 | A | 8/1982 | Uemura et al. |
| 4,376,110 | A | 3/1983 | David et al. |
| 4,421,650 | A | 12/1983 | Nagasawa et al. |
| 4,425,431 | A | 1/1984 | Takemoto et al. |
| 4,450,103 | A | 5/1984 | Konrad et al. |
| 4,460,575 | A | 7/1984 | d'Hinterland et al. |
| 4,460,683 | A | 7/1984 | Gloger et al. |
| 4,485,176 | A | 11/1984 | Bollin, Jr. et al. |
| 4,753,796 | A | 6/1988 | Moreno et al. |
| 4,766,106 | A | 8/1988 | Katre et al. |
| 4,797,474 | A * | 1/1989 | Patroni .............. C07K 1/113 530/351 |
| 4,816,567 | A | 3/1989 | Cabilly et al. |
| 4,847,325 | A | 7/1989 | Shadle et al. |
| 4,917,888 | A | 4/1990 | Katre et al. |
| 4,945,086 | A | 7/1990 | Benitz et al. |
| 4,946,778 | A | 8/1990 | Ladner et al. |
| 4,966,963 | A | 10/1990 | Patroni |
| 4,987,076 | A | 1/1991 | Takashio et al. |
| 4,992,531 | A | 2/1991 | Patroni et al. |
| 5,008,377 | A | 4/1991 | Patroni et al. |
| 5,010,183 | A | 4/1991 | Macfarlane |
| 5,114,916 | A * | 5/1992 | Shirahata et al. ............ 514/13.7 |
| 5,225,539 | A | 7/1993 | Winter |
| 5,283,317 | A | 2/1994 | Saifer et al. |
| 5,286,637 | A | 2/1994 | Veronese et al. |
| 5,362,641 | A | 11/1994 | Fuks et al. |
| 5,382,518 | A * | 1/1995 | Caput et al. ................ 435/191 |
| 5,428,128 | A | 6/1995 | Mensi-Fattohi et al. |
| 5,458,135 | A | 10/1995 | Patton et al. |
| 5,468,478 | A | 11/1995 | Saifer et al. |
| 5,529,915 | A | 6/1996 | Phillips et al. |
| 5,541,098 | A | 7/1996 | Caput et al. |
| 5,567,422 | A | 10/1996 | Greenwald |
| 5,585,089 | A | 12/1996 | Queen et al. |
| 5,612,460 | A | 3/1997 | Zalipsky et al. |
| 5,633,227 | A | 5/1997 | Muller et al. |
| 5,637,749 | A | 6/1997 | Greenwald et al. |
| 5,643,575 | A | 7/1997 | Martinez et al. |
| 5,653,974 | A | 8/1997 | Hung et al. |
| 5,766,897 | A | 6/1998 | Braxton |
| 5,811,096 | A | 9/1998 | Aleman et al. |
| 5,816,397 | A | 10/1998 | Pratt |
| 5,880,255 | A | 3/1999 | Delgado et al. |
| 5,919,455 | A | 7/1999 | Greenwald et al. |
| 5,929,231 | A | 7/1999 | Malkki et al. |
| 5,932,462 | A | 8/1999 | Harris et al. |
| 5,948,668 | A | 9/1999 | Hartman et al. |
| 5,955,336 | A | 9/1999 | Shigyo et al. |
| 6,201,110 | B1 | 3/2001 | Olsen et al. |
| 6,211,341 | B1 | 4/2001 | Zeelon et al. |
| 6,468,210 | B1 | 10/2002 | Iliff |
| 6,475,143 | B2 | 11/2002 | Iliff |
| 6,524,241 | B2 | 2/2003 | Iliff |
| 6,527,713 | B2 | 3/2003 | Iliff |
| 6,569,093 | B2 | 5/2003 | Iliff |
| 6,576,235 | B1 | 6/2003 | Williams et al. |
| 6,608,892 | B2 | 8/2003 | Shaffer et al. |
| 6,783,965 | B1 | 8/2004 | Sherman et al. |
| 6,913,915 | B2 | 7/2005 | Ensor et al. |
| 7,811,800 | B2 * | 10/2010 | Hartman et al. .............. 435/189 |
| 2002/0010319 | A1 | 1/2002 | Ansaldi et al. |
| 2003/0082786 | A1 | 5/2003 | Ensor et al. |
| 2003/0166249 | A1 | 9/2003 | Williams et al. |
| 2005/0014240 | A1 | 1/2005 | Sherman et al. |
| 2006/0188971 | A1 | 8/2006 | Hershfield et al. |
| 2007/0274977 | A1 | 11/2007 | Hartman et al. |
| 2008/0159976 | A1 | 7/2008 | Hartman et al. |
| 2009/0169534 | A1 | 7/2009 | Hartman et al. |
| 2009/0209021 | A1 | 8/2009 | Hartman et al. |

FOREIGN PATENT DOCUMENTS

| | | |
|---|---|---|
| DE | DD279486 | 3/1986 |
| DE | 279486 A1 | 6/1990 |
| EP | 0028033 A3 | 5/1981 |
| EP | 0034307 A3 | 8/1981 |
| EP | 055188 | 5/1984 |
| EP | 0204283 A2 * | 12/1986 |
| EP | 0226448 A2 | 6/1987 |
| EP | 0321134 A2 | 6/1989 |
| EP | 0408 461 A | 1/1991 |
| EP | 0408 461 A | 1/1991 |
| EP | 0727437 A2 | 8/1996 |
| EP | 1 100 542 | 5/2001 |
| JP | 55-099189 | 7/1980 |
| JP | 55-135590 | 10/1980 |
| JP | 62-055079 | 3/1987 |
| JP | 6255079 | 3/1987 |
| JP | 03-148298 | 6/1991 |
| JP | 9154581 | 6/1997 |
| JP | 09154581 | 6/1997 |
| JP | 03148208 B2 | 3/2001 |
| JP | 2005-241424 | 8/2005 |
| JP | 5599189 B2 | 10/2014 |
| KR | 333148 | 9/1994 |
| KR | 365606 | 3/1998 |
| KR | 10-0369838 | 1/2003 |
| KR | 19980069019 | 9/2003 |
| KR | 318706 | 4/2007 |
| WO | WO8604145 A1 | 7/1986 |
| WO | WO 94/19007 A1 | 9/1994 |
| WO | WO94/23735 | 10/1994 |
| WO | WO9511987 A1 | 5/1995 |
| WO | WO96/23064 | 8/1996 |
| WO | WO 98/31383 A1 | 7/1998 |
| WO | WO 00/07629 A2 | 2/2000 |
| WO | WO 00/08196 A3 | 2/2000 |
| WO | WO 01/59078 A2 | 8/2001 |
| WO | WO03045436 A1 | 6/2003 |
| WO | 2004092393 A1 | 10/2004 |
| WO | WO 2004092393 A1 * | 10/2004 |
| WO | WO 2006110761 A2 * | 10/2006 |
| WO | 2008051178 A2 | 5/2008 |

OTHER PUBLICATIONS

Carter, PNAS. Oct. 1970;67(2):620-628; abstract.*
Al-Shawi et al., (J Clin Pathol. Apr. 1983; 36(4):440-4; Abstract only).*
Sutterlin et al., (Chemosphere. Jun. 2008; 72(3):479-84; EpubApr. 24, 2008; Abstract only).*
Larsen (Prep Biochem. 1990;20(1):1-9) (Abstract Only).*
Yokoyama et al., (Enzyme Microb. Technol. Jan. 1988; 10:52-55).*
Kelly, S. J., M. Delnomdedieu, et al. (2001) as "Diabetes insipidus in uricase-deficient mice: A model for evaluating therapy with poly(ethylene glycol)-modified uricase." in J Am Soc Nephrol 12: 1001-1009.
Lee et al., (Sep. 2005) as " Arthritis & Rheumatism" in The Official Journal of the American College of Rheumatology, Abstract Supplement, vol. 52, No. 9, p. S105.
Office Action dated Jan. 26, 2010, U.S. Appl. No. 11/918,296, filed Dec. 11, 2008, Inventor Jacob Hartman.
Office Action dated Oct. 30, 2009, U.S. Appl. No. 11/899,688, Filed Sep. 7, 2007, Inventor Jacob Hartman.
Office Action dated Oct. 30, 2009, U.S. Appl. No. 11/539,475, Filed Oct. 6, 2006, Inventor Jacob Hartman.
Office Action dated Jun. 25, 2009, U.S. Appl. No. 11/539,475, Filed Oct. 6, 2006, Inventor Jacob Hartman.
Sundy, J.S. et al., A Phase I Study of Pegylated-Uricase (Puricase®) in Subjects with Gout, Arthritis Rheum. 2004 vol. 50, supplement 9, S337-338.
Sundy, J.S. et al., A Phase I Study of Pegylated-Uricase (Puricase®) in Subjects with Gout, presented at American College of Rheumatology Annual Scientific Meeting on Oct. 16-21, 2004 at San Antonio, TX, Poster 807.

(56) References Cited

OTHER PUBLICATIONS

Ganson, N.J. et al., Antibodies to Polyethylene Glycol (PEG) during Phase I Investigation of PRG-Urate Oxidase (PEG-uricase; Puricase®) for Refractory Gout, Arthritis Rheum. 2004 vol. 50, supplement 9, S338.
Ganson, N.J. et al., Antibodies to Polyethylene Glycol (PEG) during Phase I Investigation of PEG-Urate Oxidase (PEG-uricase; Puricase®) for Refractory Gout, presented at American College of Rheumatology Annual Scientific Meeting on Oct. 16-21, 2004 at San Antonio, TX, Poster 808.
Baraf H. et al., Resolution of Tophi With Intravenous Peg-uricase in Refractory Gout, Arthritis & Rheumatism, 2005, Sep Supplement, vol. 52, No. 9, p. S105.
Baraf H. et al., Resolution of Tophi With Intravenous Peg-uricase In Refractory Gout, presented at American College of Rheumatology 2005 Annual Scientific Meeting on Nov. 13-17, 2005 at San Diego, CA, Poster 194.
Sundy, J.S. et al., A Phase 2 Study of Multiple Doses of Intravenous Polyethylene Glycol (PEG)-uricase in Patients with Hyperuricemia and Refractory Gout, presented at American College of Rheumatology 2005 Annual Scientific Meeting on Nov. 13-17, 2005 at San Diego, CA, #1836.
Delgado et al., "The Uses and Properties of PEG-Linked Proteins," Critical Reviews in Therapeutic Drug Carrier Systems, 9(3,4):249-304 (1992).
Streuli et al., "Target cell specificity of two species of human interferon-a produced in *Escherichia coli* and of hybrid molecules derived from them," Proc. Natl. Acad. Sci. USA, vol. 85, pp. 5879-5883, Aug. 1988.
Huston et al., "Protein engineering of antibody binding sites: Recovery of specific activity in an anti-digoxin single-chain Fv analogue produced in *Escherichia coli*," Proc. Natl. Acad. Sci. USA, vol. 85, pp. 5879-5883, Aug. 1988.
Kozbor et al., "The production of monoclonal antibodies from human lymphocytes," Immunology Today, vol. 4, No. 3, p. 72, 1983.
Scandella et al., "A Membrane-Bound Phospholipase AI Purified from *Escherichia colt*," Biochemistry, vol. 10, No. 24, p. 4447, 1971.
Macart et al., "An improvement of the Coomassie Blue dye binding method allowing an equal sensitivity to various proteins: application to cerebrospinal fluid," Clinica Chimica Acta, 122 (1982) 93-101, Elsevier Biomedical Press.
Nagata et al., "Synthesis in *E. coli* of a polypeptide with human leukocyte interferon activity," Nature, vol. 284, p. 316, Mar. 27, 1980.
Derynck et al., "Expression of human fibroblast interferon gene in *Escherichia coli*," Nature, vol. 287, p. 193-197, Sep. 18, 1980.
Goeddel et al., "Human leukocyte interferon produced by *E. coli* is biologically active," Nature, vol. 287, p. 411, Oct. 2, 1980.
Neuberger et al., "Recombinant antibodies possessing novel effector functions," Nature, vol. 312, p. 604-608, Dec. 13, 1984.
Takeda et al., "Construction of chimaeric processed immunoglobulin genes containing mouse variable and human constant region sequences," Nature, vol. 314, p. 452-454, Apr. 4, 1985.
Ward et al., "Building activities of a repertoire of single immunoglobulin variable domains secreted from *Escherichia coli*," Nature, vol. 341, p. 544-546, Oct. 12, 1989.
Ben-Bassat et al., "Processing of the Initiation Methionine from Proteins: Properties of the *Escherichia coli* Methionine Aminopeptidase and Its Gene Structure," Journal of Bacteriology, vol. 169, No. 2, p. 751-757, Feb. 1987.
Cole et al., "The EBV-Hybridoma Technique and Its Application to Human Lung Cancer," Monoclonal Antibodies and Cancer Therapy, pp. 77-96, 1985.
Morrison et al., "Chimeric human antibody molecules: Mouse antigen-binding domains with human constant-region domains," Proc. Natl. Acad. Sci. USA, vol. 81, pp. 6851-6855, Nov. 1984.

Kohler et al., "Continuous cultures of fused cells secreting antibody of predefined specificity," Nature, vol. 256, p. 495-497, Aug. 7, 1975.
Yelverton et al., "Bacterial synthesis of a novel human leukocyte interferon," Nucleic Acids Research, vol. 9, No. 3, p. 731,1981.
Cote et al., "Generation of human monoclonal antibodies reactive with cellular antigens," Proc. Natl. Acad.Sci. USA, vol. 80, p. 2026-2030, Apr. 1983.
Bird et al., "Single-Chain Antigen-Binding Proteins," Science, vol. 242, p. 423-426, Oct. 21, 1988.
Huse et al., "Generation of a Large Combinatorial Library of the Immunoglobulin Repertoire in Phage Lambda," Science, vol. 246, p. 1275-1281, Dec. 8, 1989.
Kabat et al., "Sequences of Proteins of Immunological Interest," US Dept. of Health and Human Services, 1983.
Abuchowski, A., et al. "Effect of Covalent Attachment of Polyethylene Glycol on Immunogenicity and Cirulating Life of Bovine Liver Catalase." J. Biol. Chem. 252-:3582-3586, American Society for Biochemistry and Molecular Biology (1977).
Abuchowski, A., et al., "Reduction of Plasma Urate Levels in the Cockerel with Polyethylene Glycol-Uricase," J. Pharmacol. Exp. Ther. 219:352-354, The American Society for Pharmacology and Experimental Therapeutics (1981).
Alvares, K., et al., "The Nucleotide Sequence of a Full Length cDNA Clone Encoding Rat Liver Urate Oxidase," Biochem. Biophys. Res. Commun. 158:991-995, Academic Press, Inc. (1989).
Alvares, K., et al., "Rat urate oxidase produced by recombinant baculovirus expression: Formation of peroxiscome crystallized core-like structures," Proc. Natl. Acad. Sci. USA 89:4908-4912, National Academy of Sciences (1992).
Braun, A. and Alsenz, J., "Development and Use of Enzyme-Linked Immunosorbent Assays (ELISA) for the Detection of Protein Aggregates in Interferon-Alpha (IFN-α) Formulations," Pharm. Res. 14:1394-1400, Plenum Publishing Corporation (Oct. 1997).
Braun, A., et al. "Protein Aggregates Seem to Play a Key Role Among the Parameters Influencing theAntigenicity of Interferon Alpha (IFN-α) in Normal and Transgenic Mice," Pharm. Res. 14:1472-1478, Plenum Publishing Corporation (Oct. 1997).
Burnham, N.L., "Polymers for delivering peptides and proteins," Am. J. Hosp. Pharm. 51:210-218, American Society of Hospital Pharmacists, Inc. (1994).
Caliceti, P., et al., "Biopharmaceutical Properties of Uricase Conjugated to Neutral and Amphiphilic Polymers," Bioconjugate Chem. 10:639-646, American Chemical Society (Jul.—Aug. 1999).
Chen, R.H.-L., et al., "Properties of Two Urate Oxidases Modified by the Covalent Attachment of Poly(Ethylene Glycol)," Biochem. Biophys. Acta 660:293-298, Elsevier/North Holland Biomedical Press (1981).
Chua, C.C., et al., "Use of Polyethylene Glycol-Modified Uricase (PEG-Uricase) to Treat Hyperuricemia in a Patient with Non-Hodgkin Lymphoma," Ann. Intern. Med. 109:114-117, American College of Physicians (1988).
Colloc'h, N., et al., "Crystal Structure of the protein drug urate oxidase-inhibitor complex at 2.05 A resolution," Nature Struct. Biol. 4:947-952, Nature Publishing Company (Nov. 1997).
Conley, T.G., and Priest, D.G., "Thermodynamics and Stoicheiometry of the Binding of Substrate Analogues to Uricase," Biochem. J. 187:727-732, The Biochemical Society (1980).
Davis, F.F., et al., "Enzyme-Polyethylene Glycol Adducts: Modified Enzymes with Unique Properties," in: Enzyme Engineering, vol. 4, Braun, G.B., et al., eds., Plenum Press, New York, pp. 169-173 (1978).
Davis, S., et al., "Hypouricaemic Effect of Polyethyleneglycol Modified Urate Oxidase," Lancet 2:281-283, Lancet Publishing Group (1981).
Donadio, D., et al., "Manifestation de type anaphylactique après injection intra-veineuse d'urate-oxydase chez un enfant asthmatique atteint de leucèmie aiguë," La Nouv. Presse Med. 10:711-712, Masson (1981).
Unverified English language partial translation of Donadio, D., et al., "Anaphylaxis-like manifestations after intravenous injection of urate oxidase in an asthmatic child with acute leukemia," La Nouv. Presse Med. 10:711-712, Masson (1981) (Document NPL15).

(56) References Cited

OTHER PUBLICATIONS

Fam, A.G., "Strategies and Controversies in the Treatment of Gout and Hyperuricaemia," Ballière's Clinical Rheumatology 4:177-192, Ballière's Clinical Rheumatology 4:177-192, Ballière Tindall (1990).

Fridovich, I., "The Competitive Inhibition of Uricase by Oxonate and by Related Derivatives of s-Triazines," J. Biol. Chem. 240:2491-2494, American Society for Biochemistry and Molecular Biology (1965).

Fuertges, F., and Abuchowski, A., "The Clinical Efficacy of Poly(Ethylene Glycol)-Modified Proteins," J. Control. Release 11:139-148, Elsevier Science (1990).

Fujita, T., et al., "Tissue Distribution of 111 In-Labeled Uricase Conjugated with Charged Dextrans and Polyethylene Glycol," J. Pharmacobio-Dyn. 14:623-629, Pharmaceutical Society of Japan (1991).

Greenberg, M.L. and Hershfield, M.S., "A Radiochemcial-High-Performance Liquid Chromatographic Assay for Urate Oxidase in Human Plasma," Anal. Biochem. 176:290-293, Academic Press, Inc. (1989).

Hande, K.R., et al., "Severe Allpurinol Toxicity. Description and Guidelines for Prevention in Patients with Renal Insufficiency," Am. J. Med. 76:47-56, Excerpta Medica (1984).

Hedlund, L.W., et al., "Magnetic Resonance Microscopy of Toxic Renal Injury Induced by Bromoethylamine in Rats," Fundam. Appl. Toxicol. 16:787-797, Academic Press (1991).

Henney, C.S. and Ellis, E.F., "Antibody Production to Aggregated Human γG-Globulin in Acquired Hypogammaglobulinemia," New Engl. J. Med. 278:1144-1146, Massachusetts Medical Society (1968).

Herbst, R., et al., "Folding of Firefly (Photinus pyralis) Luciferase: Aggregation and Reactivation of Unfolding Intermediates," Biochem. 37:6586-6597, American Chemical Society (May 1998).

Hershfield, M.S., et al., "Use of Site-Directed Mutagenesis to Enhance the Epitope-shielding Effect of Covalent Modification of Proteins with Polyethylene Glycol," Proc. Natl. Acad. Sci. USA 88:7185-7189, Natinal Academy of Sciences (1991).

Ishino, K. and Kudo, S., "Proteins Concentration Dependence on Aggregation Behavior and Properties of Soybean 7S and 11S Globulins during Alkali-treatment," Agric. Biol. Chem. 44:1259-1266, Agricultural Chemical Society of Japan (1980).

Ito, M., et al., "Identification of an Amino Acid Residue Involved in the Substrate-binding Site of Rat Liver Uricase by Site-directed Mutagenesis," Biochem. Biophys. Res. Commun. 187:101-107, Academic Press (1992).

Kahn, K., and Tipton, P.A., "Kinetic Mechanism and Cofactor Content of Soybean Root Nodule Rate Oxidase," Biochemistry 36:4731-4738, American Chemical Society (Apr. 1997).

Kelly, S.J., et al., "Diabetes Insipidus in Uricase-Deficient Mice: A Model for Evaluating Therapy with Poly (Ethylene Glycol)-Modified Uricase," J. Am,. Soc. Nephrol. 12:1001-1009, Lippincott Williams & Wilkins (May 2001).

Kito, M., et al., "A Simple and Efficient Method for Preparation of Monomethoxopolyethylene Glycol Activated with p-Nitrophenylchlorformate and Its Application to Modiciation of L-Asparanginase," J. Clin. Biochem. Nutr. 21:101-111, Institute of Applied Biochemistry (1996).

Kunitani, M., et al., "On-line characterization of polyethylene glycol-modified proteins," J. Chromat. 588:125-137, Elsevier Science Publishers B.V. (1991).

Kunitani, M., et al., "Classical light scattering quantitaiton of protein aggregates: off-line spectroscopy versus HPLCc detection," J. Pharm. Biomed. Anal. 16:573-586, Elsevier Science B.V. (Dec. 1997).

Leach, M. et al., "Efficacy of Urate Oxidase (Uricozyme) in Tumour Lysis Induced Urate Nephropathy," Clin. Lab. Haematol. 20:169-172, Blackwell Scientific Publications (Jun. 1998).

Lee, C.C., et al., "Generation of cDNA Probes Directed by Amino Acid Sequence: Cloning of Urate Oxidase," Science 239:1288-1291, American Association for th eAdvancement of Science (1988).

Legoux, R. et al., "Cloning and Expression in *Escherichia coli* of the Gene Encoding Aspergillus flavus Urate Oxidase," J. Biol. Chem. 267:8565-8570, American Society for Biochemistry and Molecular Biology (1992).

Madmoud, H.H., et al., "Advances in the Management of Malignancy-Associated Hyperuricaemia," Br. J. Cancer (Supplement 4) 77:18-20, Churchill Livingstone (Jun. 1998).

Mahler, H.R., et al., "Studies of Uricase, I. Preparation, Purification, and Properties of a Cuproprotein," J. Biol. Chem. 216:625-641, American Society for Biochemistry and Molecular Biology (1955).

Mourad G. et al., Presse Med. 1984, 13 (42):2585.

Malakhova, E.A., et al., "Kinetic Properties of Bacterial Urate Oxidase Entrapped in Hydrated Reversed Micelles," Biologicheskie Membrany 8:453-459, Nauka (1991).

Mirua, S., et al., "Urate Oxidase in Imported into Peroxisomes Recognizing the C-terminal SKL Motif of Proteins," Eur. J. Biochem. 223:141-146, Blackwell Science Ltd. (1994).

Monkarsh, S.P., et al., "Positional Isomers of Monopegylated Interferon α-2a: Isolation, Characterization, and Biological Activity ," Analytical Biochemistry 247:434-440, Academic Press (1997).

Montalbini, P., et al., "Uricase form leaves: its purification and characterization from three different higher plants," Planta 202:277-283, Springer-Verlag (Jun. 1997).

Moore, W.V. and Leppert, P., "Role of Aggregated Human Growth Hormone (hGH) in Development of Antibodies to hGH," J. Clin. Endocrinol. Metab. 51:691-697, The Endocrine Society (1980).

Nishida, Y., et al., "Hypouricaemic effect after oral administration in chickens of polyethylene glycol-modified uricase entrapped in liposomes," J. Pharm. Pharmacol. 36:354-355, Pharmaceutical Press (1984).

Nishimura, H., et al., "Modification of Yeast Uricase with Polyethlene Glycol: Disappearance of Binding Ability towards Anti-Uricase Serum," Enzyme 24:261-264, Karger (1979).

Nishimura, H., et al., "Improved Modification of Yeast Uricase with Polyethylene Glycol, Accompanied with Nonimmunoreactivity Towards Anti-Uricase Serum and High Enzymic Activity," Enzyme 26:49-53, Karger (1981).

Nucci, M.L., et al., "The Therapeutic Value of Poly(Ethylene Glycol)-Modified Proteins," Adv. Drug Deliv. Rev. 6:133-151, Elsevier Science Publishers (1991).

Osman, A.M., et al., "Liver Uricase in Camelus dromedarius: Purification and Properties," Comp. Biochem. Physiol. 94B:469-474, Pergamon Press Plc. (1989).

Palleroni, A.V., et al., "Interferon Immunogenicity: Preclinical Evaluation of Interferon-α2a," J. Interferon Cyto. Res. 17:S23-S27, Mary Ann Liebert, Inc. (Jul. 1997).

"PEG-Uricase BioTechnology General, Duke University, Mountain View licensing agreement," R&D Focus Drug News, Accession No. 1998-2984, available on Datastar File IPNR/IPNA, (Aug. 1998).

Porstmann, B., et al., "Comparision of Chromogens for the Determination of Horseradish Peroxidase as a Marker in Enzyme Immunoassay," J. Clin. Chem. Clin. Biochem. 19:435-439, Walter de Gruyter & Co. (1981).

Pui, C-H., et al., "Urate oxidase in prevention and treatment of hyperuricemia associated with lymphoid malignancies," Leukemia 11:1813-1816, Stockton Press (Nov. 1997).

Saifer, M.G.P., et al., "Plasma Clearance and Immunologic Properties of Long-Acting Superoxide Dismutase Prepared Using 35,000 to 120,000 Dalton Poly-Ethylene Glycol," in: Free Radicals in Diagnostic Medicine, Armstrong, D., ed., Plenum Press, New York, NY, pp. 377-387 (1994).

Saifer, M.G.P., et al., "Improved Conjugation of Cytokines Using High Molecular Weight Poly(ethylene glycol): PEG-GM-CSF as a Prototype," Polymer Prepr. 38:576-577, American Chemical Society (Apr. 1997).

Sartore, L., et al., "Enzyme Modification by MPEG with an Amino Acid or Peptide as Spacer Arms," Appl. Biochem. Biotechnol. 27:45-54, Humana Press (1991).

(56) References Cited

OTHER PUBLICATIONS

Savoca, K.V., et al., "Induction of Tolerance in Mice by Uricase and Monomethoxypolyethylene Glycol-Modified Uricase," Int. Archs. Allergy appl. Immun. 75:58-67, Karger (1984).

Shearwater Polymers Inc., "Functionalized biocompatible Polymers for Research and Pharmaceuticals," in: Shearwater Polymers, Inc., Catalog, pp. 27, 47, and 48. (Jul. 1997).

Sherman, M.R., et al., "Conjugation of High-Molecular Weight Poly(ethyleneglycol) to Cytokines: Granulocyte-Macrophage Colony-Stimulating Factors as Model Substrates," in:ACS Symposium Series 680. Poly(ethylene glycol). Chemistry and Biological Applications, Harris, J.M. and Zalipsky. S., eds., American Chemical Society, Washington, DC, pp. 155-169 (Apr. 1997).

Somack, R., et al., "Preparation of Long-Acting Superoxide Dismutase Using High Molecular Weight Polyethylene Glycol (41,000-72,000 Daltons)," Free Rad. Res. Comms. 12-13:553-562, Harwood Academic Publishers GmbH (1991).

Suzuki, H. and Verma, D.P.S., "Soybean Nodule-Specific Uricase (Nodulin-35) is Expressed and Assembled into a Functional Tetrameric Holoenzyme in *Escherichia coli*," Plant Physiol. 95:384-389, American Society of Plant Physiologists (1991).

Treuheit, M.J., et al., "Inverse Relationship of Protein Concentration and Aggregation," Pharm. Res. 19:511-516, Plenum Publishing Corporation (Apr. 2002).

Tsuji, J.-I., et al., "Studies on Antigenicity of the Polyethylene Glycol (PEG)-Modified Uriacse," Int. J. Immunopharmacol. 7:725-730, Elsevier Science (1985).

Venkataseshan, V.S., et al., "Acute Hyperuricemic Nephropathy and Renal Failure after Transplantation," Nephron 56:317-321, Karger AG (1990).

Veronese, F.M., et al., "Surface Modification of Proteins. Activation of Monomethoxy-Polyethylene Glycols by Phenylchloroformates and Modification of Ribonuclease and Superoxide Dismutase," Appl. Biochem. Biotechnol. 11:141-152, The Humana Press, Inc. (1985).

Veronese, F.M., et al., "New Synthetic Polymers for Enzyme and Liposome Modification," in: ACS Symposium Series 680, Poly(Ethylene Glycol) Chemistry and Biological Applications, Harris, J.M., and Zalipsky, S., eds., American Chemical Society, Washington, D.C. pp. 182-192 (Apr. 1997).

Wallrath, L.L., et al., "Molecular Characterization of the Drosophila melanogaster Urate Oxidase Gene, an Ecdysone-Repressible Gene Expressed Only in the Malpighian Tubules," Molec. Cell. Biol. 10:5114-5127, American Society for Microbiology (1990).

Wang, X., et al., "Rat urate oxidase: cloning and structural analysis of the gene and 5'-flanking region," Gene 97:223-229, Elsevier Science Publishers B.V. (1991).

Wu, X., et al., "Urate oxidase: Primary structure and evolutionary implications," Proc. Natl. Acad. Sci. USA 86:9412-9416, National Academy of Sciences (1989).

Wu, X., et al., "Two Independent Mutational Events in the Loss of Urate Oxidase during Hominoid Evolution," J. Mol. Evol. 34:78-84, Springer-Verlag (1992).

Wu, X., et al., "Hyperuricemia and urate nephropathy in urate oxidase-deficient mice," Proc. Natl. Acad. Sci. USA 91:742-746, National Academy of Sciences (1994).

Yasuda, Y., et al., "Biochemcial and Biopharmaceutical Properties of Macromolecular Conjugates of Uricase with Dextran Polyethylene Glycol," Chem. Pharm. Bull. 38:2053-2046, Pharmaceutical Society of Japan (1990).

Yeldandi, A.V., et al., "Human Urate Oxidase Gene: Cloning and Partial Sequence Analysis Reveal a Stop Codon within the Fifth Exon," Biochem. Biophys. Res. Commun. 171:641-646, Academic Press (1990).

U.S. Trademark Registration No. 2,246,623, entitled "Puricase," filed Jul. 15, 1997.

ESP@cenet database, Unverified English language abstract for JP 09-154581 (Document FP6).

NCBI Entrez, GenBank Report, Accession No. NP_446220, Wang, X.D., et al. (Oct. 2004).

Patent Abstracts of Japan, Unverified English language abstract for JP-55-099189 (Document FPI).

Patent Abstracts of Japan, Unverified English language abstract for JP 62-055079 (Document FP2).

Patent Abstracts of Japan, Unverified English language abstract for JP 03-148298 (Document FP4).

S. Sundy et al., Arthritis & Rheumatism, vol. 52, No. 9 (Supplement), Sep. 2005, Abstract Supplement, 2005 annual Scientific Meeting, Nov. 12-17, 2005, San Diego, California; 1836.

Michael A. Becker, Hyperuricemia and Gout, In: The Metabolic and Molecular Bases of Inherited Disease. Edited by Scriver CR, Beaudet AL, Sly WS, Valle D, 8th edn. New York; McGraw-Hill; 2001: 2513-2535.

Terkeltaub RA: Clinical practice. Gout. N. Engl. J. Med. 2003, 349(17): 1647-1655.

Wortmann RL et al.: Gout and Hyperuricemia. In: Kelley's Textbook of Rheumatology. Edited by Ruddy S, Harris Ed, Jr., Sledge CB, 6th edn. St. Louis: W.B. Saunders: 2001: 1339-1371.

Li-Yu J et al., Treatment of Chronic Gout.. Can We Determine When Urate Stores Are Depleted Enough to Prevent Attacks of Gout?, J. Rheumatol 2001, 28(3):577-580.

Perez-Ruiz F. et al., Effect of Urate-Lowering Therapy on the Velocity of Size Reduction of Tophi in Chronic Gout, Arthritis Rheum. 2002, 47(4); 356-360.

Shoji A. et al., A Retrospective Study of the Relationship Between Serum Urate Level and Recurrent Attacks of Gouty Arthritis: Evidence for Reduction of Recurrent Gouty Arthritis With Antihyperuricemic Therapy, ; arthritis Rheum. 2004, 51(3):321-325.

Coiffier B. et al., Efficacy and Safety of Rasburicase (recombinant urate oxidase) for the Prevention and Treatment of Hyperuricemia During Induction Chemotherapy of Aggressive Non-Hodgkin's Lymphoma: Results of the GRAAL1 Study; J. Clin. Oncol. 2003, 21(23):4402-4406.

Goldman SC et al., A Randomized Comparison Between Rasburicase and Allopurinol in Children with Lymphoma or Leukemia at High Risk for Tumor Lysis, Blood 2001, 97 (10): 2998-3303.

Kissel P. et al., Modificaiton of Uricaemia and the Excretion of Uric Acid Nitrogen by an Enzyme of Fungal Origin, Nature 1968, 217: 72-74.

London M. et al., Uricolytic Activity of Purified Uricase in Two Human Beings, Science 1957, 125:937-938.

Montagnac R. et al. Nephrologie 1990, 11 (4):259.

Moolenburgh JD et al., Rasburicase Treatment in Severe Tophaceous Gout: a Novel Therapeutic Option, Clin. Rheumatol 2005: 1-4.

Richette P. et al., Successful Treatment with Rasburicase of a Tophaceous Gout in a Patient Allergic to Allopurinol, Nature Clinical Practice Rheumatology 2006, 2(6):338-342.

Harris JM et al., Effect of Pegylation on Pharmaceuticals, Nat. Rev. Drug Discov. 2003, 2(3):214-221.

Veronese FM et al., Introduction and Overview of Peptide and Protein Pegylation, Advanced Drug Delivery Reviews 2002, 54(4):453-456.

Kelly SJ et al., Diabetes Insipidus in Uricase-Deficient Mice: A Model for Evaluating Therapy with Poly(Ethylene Glycol)-Modified Uricase, Journal of American Society of Nephrology 2001, 12:1001-1009.

Ganson J. et al., Control of Hyperuricemia in Subjects with Refractory Gout, and Induction of antibody Against Poly(ethylene glycol) (PEG), in a Phase I Trial of Subcutaneous Pegylated Urate Oxidase, Arthritis Res Ther 2005, 8(1):R12.

Motojima, K. et al., Cloning and Sequence Analysis of cDNA for Rat Liver Uricase, J. Biol. Chem. 263:16677-16681, American Society for Biochemistry and Molecular Biology (1988).

Sigma Catalog pg. 1002, Product Nos. U 3250, 292-8, U3500, U9375, or U3377 (1993).

Kontsek et al., Forty Years of Interferon, 1997, Acta Virologica, vol. 41, pp. 349-352.

European Examination Report for related European Application No. 01 923 265.1 mailed Dec. 13, 2007, European Patent Office, Munich, DE.

(56) References Cited

OTHER PUBLICATIONS

Office Action mailed on Sep. 11, 2003; in related U.S. Appl. No. 09/839,946, Williams et al., filed Apr. 19, 2001.
Office Action mailed on Mar. 5, 2004; in related U.S. Appl. No. 09/839,946, Williams et al., filed Apr. 19, 2001.
Office Action mailed on Aug. 2, 2004; in related U.S. Appl. No. 09/839,946, Williams et al., filed Apr. 19, 2001.
Office Action mailed on Jan. 26, 2005; in related U.S. Appl. No. 09/839,946, Williams et al., filed Apr. 19, 2001.
Office Action mailed on Jul. 20, 2005; in related U.S. Appl. No. 09/839,946, Williams et al., filed Apr. 19, 2001.
Advisory Action mailed on Dec. 5, 2005; in related U.S. Appl. No. 09/839,946, Williams et al., filed Apr. 19, 2001.
Examiner's Answer to Appeal Brief mailed on Jul. 11, 2006; in related U.S. Appl. No. 09/839,946, Williams et al., filed Apr. 19, 2001.
BPAI Decision decided on Jul. 18, 2007; in related U.S. Appl. No. 09/839,946, Williams et al., filed Apr. 19, 2001.
"Chromatography," Practical Application, ed E. Heftman, part 1, Moscow, "Mir," 1986, pp. 104, 108-109.
Becker MA, et al. N. Engl. J. Med. 2005, 353(23): 2450-2461.
Emmerson BT, N. Engl. J. Med. 1996, 334:445-451.
Forrest A., Hawtoff J., Egorn MJ; Evaluation of a New Program for Population PK/PD Analysis Applied to Simulated Phase I Data. Clinical Pharmacology and Therapeuticas 49 (2): 153, 1991.
Yamanaka H., et al., Adv. Exp. Med. Biol. 1998, 431:13-18.
Leaustic M. et al., 1983, Rev. Rhum. Mal. Osteoartic 50:553-554.
Potaux, L. et al., 1975, Nouv. Presse Med. 4:1109-1112.
Ben-Bassat and Bauer,1987, Nature 326:315.
Otte and Bertini, 1975, Acta Physiol. Latinoam, 25:451-457.
Truscoe, 1967, Enzymologia 33:1 19-32.
Antonopoulos et al., 1961, Biochim. Biophys. Acta 54:213-226.
Embery, 1976, J. Biol. Buccale 4:229-236.
Rinella et al., 1998, J. Colloid Interface Sci. 197:48-56.
Maccari and Volpi, 2002, Electrophoresis 23:3270-3277.
Scott, 1955, Biochim. Biophys. Acta 18:428-429.
Scott, 1960, Methods Biochem. Anal. 8:145-197.
Laurent et al., 1960, Biochim. Biophys. Acta 42:476-485.
Scott, 1961, Biochem. J. 81:418-424.
Pearce and Mathieson, 1967, Can. J. Biochemistry 45:1565-1576.
Lee, 1973, Fukushima J. Med. Sci. 19:33-39.
Saito, 1955, Kolloid-Z 143:66.
Blumberg and Ogston, 1958, Biochem. J. 68:183-188.
Matsumura et al., 1963, Biochim, Biophys. Acta 69:574-576.
Serafini-Fracassini et al., 1967, Biochem. J. 105:569-575.
Smith et al., 1984, J. Biol. Chem. 259:11046-11051.
Hascall and Heinegard, 1974, J. Biol. Chem. 249:4232-4241, 4242-4249, and 4250-4256.
Heinegard and Hascall, 1974, Arch. Biochem. Biophys. 165:427-441.
Lee et al., 1992, J. Cell Biol. 116: 545-557.
Varelas et al., 1995, Arch. Biochem. Biophys. 321:21-30.
LB Jaques, 1943, Biochem. J. 37:189-195.
AS Jones, 1953, Biochim. Biophys. Acta 10:607-612.
JE Scott, 1955, Chem. and Ind. 168-169.
Cooper JF, 1990, J. Parenter Sci. Technol. 44:13-5.
Kozma et al., 2000, Mol. Cell. Biochem., 203:103-112.
Montalbini, P. et al., Isolation and characterization of uricase from bean leaves and its comparison with uredospore enzymes, Plant Sci. 147:139-147, Elsevier Science Ireland Ltd. (May 1999).
Cristina Delgado, Gillian E. Francis, and Derek Fisher; "The Uses and Properties of PEG-Linked Proteins," Molecular Cell Pathology Laboratory, Royal Free Hospital School of Medicine, London, UK., Critical Review in Therapeutic Drug Carrier Systems, 9 (3, 4): 249-304 (1992).
Fred Sherman et al., "Methionine or Not Methionine at the Beginning of a Protein," BioEssays, vol. 3, No. 1, pp. 27-31, 1985.
Tianxi Zhang et al., "Affinity Extraction of BSA with Reversed Micellar System Composed of Unbound Cibacron Blue," Biotechnology Progress, vol. 15, Issue 6, pp. 1078-1082, 1999.

Michael S. Hershfield, Biochemistry and Immunologly of Poly(ethylene glycol)-Modified Adenosine Deaminase (PEG-ADA), in ACS Symposium Series, Harris J.M. and S. Zalipsky Eds., American Chemical Society, 145-154, 1997.
Saifer, M., et al., Plasma Clearance and Immunologic Properties of Long-Acting Superoxide Dismutase Prepared Using 35,000 to 120,000 Dalton Poly-Ethylene Glycol, in Free Radicals in Diagnostic Medicine, Armstrong, D. Ed., Plenum Press, New York, 366:377-387, 1994.
Brenda Enzyme Database: E.C. 1.7.3.3, Urate Oxidase, available via internet www.brenda-enzymes.info, Mar. 27, 2008.
"Purification and Molecular Properties of Urate Oxidase from Chlamydomonas Reinhardtii," Josefa M. Alamillo, Jacobo Cardenas and Manuel Pineda, 1991 Elsevier Science Publishers B.V. (Biomedical Divisiona), Biochimica et Biophysica Acta, 1076 (1991) 203-208.
Hortnagl, H., et al., "Membrane Proteins of Chromaffin Granules, Dopamine-hydroxylase, a Major Constituent," The Biochemical Journal vol. 129, No. 1, 187-195 (1972).
Crivelli, E. et al., "A Single Step Method for the Solubilization and Refolding of Recombinant Protein from E. coli Inclusion Bodies" Australian Journal of Biotechnology vol. 5, No., 2, 78-80, 86 (1991).
Sadaji Yokoyama et al., "Rapid Extraction of Uricase from Candida utilis Cells by Use of Reducing Agent Plus Surfactant," Enzyme Microb. Technol. vol. 10, pp. 52-22 (1988).
Singapore Search Report Application No. 201102592-1, Date of mailing, Jul. 6, 2012, by Hungarian Intellectual Patent Office.
Becker et al., "Activation of Hydroxylic Polymers—by Reaction with Carbonate or Chlorofornnate Ester in Presence", English Abstract, Derwent World Patents Index, Accession No. 8448552, (2004).
Bossavy, J.P. et al., "Comparison of the Antithrombotic Effect of PEG-Hirudin and Heparin in a Human Ex Vivo Model of Arterial Thrombosis." (1999) Arterioscler. Thromb. Vasc. Biol., vol. 19, pp. 1348-1353.
Clark, R. et al., "Long-acting Growth Hormones Produced by Conjugation with Polyethylene Glycol." (1996) The Journal of Biological Chemistry, vol. 271, No. 36, pp. 21969-21977.
EC Number commentary 1.7.3.3 from the Brenda Enzyme Database at www.brenda-enzymes.info> accessed on Mar. 27, 2008.
Francis, G.E. et al., "PEGylation of cytokines and other therapeutic proteins and peptides: the importance of biological optimisation of coupling techniques." (1998) International Journal of Hematology, vol. 68, pp. 1-18.
Gaertner, H.F. et al., "Site-Specific Attachment of Functionalized Poly(ethylene glycol) to the Amino Terminus of Proteins," (1996) Bioconjugate Chem., vol. 7, pp. 38-44.
Hazen, J., "Adjuvants—Terminology, Classification, and Chemistry" (2000) Weed Technology, vol. 14:773-784.
Heftmann et al., "Chromatography: fundamentals and applications of chromatography and electrophoretic methods. Part A: fundamentals and techniques." (1983) Journal of Chromatography, vol. 22A, pp. A104-A110.
Hershfield, "Biochemistry and Immunology of Poly(ethylene glycol)-Modified Adenosine Deaminase (PEG-ADA)", American Chemical Society, pp. 145-154, (1997).
Hinds, K. et al., "Synthesis and Characterization of Poly(ethylene glycol)-Insulin Conjugates." Bioconjugate Chem., vol. 11., pp. 195-201.
Inada, Y. et al., "Biomedical and biotechnological applications of PEG- and PM-modified proteins." (1995) TIBTECH, vol. 13, pp. 86-91.
International Preliminary Report on Patentability dated Nov. 4, 2005.
International Search Report and Written Opinion for PCT/US2006/013751 dated Sep. 6, 2006.
Kinstler, O.B. et al., "Characterization and Stability of N-terminally PEGylated rhG-CSF." (1996) Pharmaceutical Research, vol. 13, No. 7, pp. 996-1002.
Moolenburgh, J.D. et al, "Rasburicase treatment in severe tophaceous gout: a novel therapeutic option." (2006) Clin. Rheumatol., vol. 25, pp. 749-752.

(56) References Cited

OTHER PUBLICATIONS

Pitts, O.M. et al., "Uricase. Subunit Composition and Resistance to Denaturants." (1974) Biochemistry, vol. 13, No. 5, pp. 888-892.
Saifer et al., "Plasma Clearance and Immunologic Properties of Long-Acting Superoxide Dismutase Prepared Using 35,000 to 120,000 Dalton Poly-Ethylene Glycol", Free Radicals in Diagnostic Medicine, pp. 377-387, (1994).
Sakane, T. et al., "Carboxyl-directed Pegylation of Brain-derived Neurotrophic Factor Markedly Reduces Systemic Clearance with Minimal Loss of Biologic Activity." (1997) Pharmaceutical Research, vol. 14, No. 8, pp. 1085-1091.
Search Report for Application No. 201102592-1, dated Jun. 7, 2012.
Sherman et al., "Methionine or Not Methionine at the Beginning of a Protein", Bio Essays, vol. 3, No. 1, pp. 21-31, (1985).
Tomanee, P. et al., "Fractionation of Protein, RNA, and Plasmid DNA in Centrifugal Precipitation Chromatography Using Cationic Surfactant CTAB Containing Inorganic Salts NaCl and NH4Cl." (2004) Published online Sep. 9, 2004 in Wiley InterScience. DOI: 10.1002/bit.20203.
Written Opinion on Application No. 201102592-1 dated Nov. 21, 2013.
Yokoyama, S. et al., "Rapid extraction of uricase from Candida utilis cells by use of reducing agent plus surfactant." (1988) Enzyme Microb. Technol., vol. 10, January.
Zhang, W. et al., "Forward and backward extraction of BSA using mixed reverse micellar system of CTAB and alkyl halides." (2002) Biochemical Engineering Journal 12 (2002) 1-5.

\* cited by examiner

| No. | RT | Area | Height | Conc I | BC |
|---|---|---|---|---|---|
| 1 | 15.01 | 2358734 | 63671 | 15.788 | FWD |
| 2 | 15.10 | 315443 | 63515 | 2.111 | FWD |
| 3 | 15.18 | 436417 | 62665 | 2.921 | FWD |
| 4 | 15.30 | 285062 | 62077 | 1.908 | FWD |
| 5 | 15.45 | 434310 | 62122 | 2.907 | FWD |
| 6 | 15.49 | 2800622 | 62094 | 18.746 | FWD |
| 7 | 21.80 | 1375688 | 10369 | 9.208 | FWD |
| 8 | 25.53 | 6933862 | 70529 | 46.411 | FWD |
|  |  | 14940138 | 457042 | 100.000 |  |

| No. | RT | Area | Height | Conc I | BC |
|---|---|---|---|---|---|
| 1 | 15.34 | 48627 | 580 | 0.942 | FWD |
| 2 | 21.80 | 377396 | 3941 | 7.315 | FWD |
| 3 | 25.50 | 4733378 | 56069 | 91.743 | FWD |
|  |  | 5159401 | 60590 | 100.000 |  |

PURIFICATION OF PROTEINS WITH CATIONIC SURFACTANT

CROSS REFERENCE TO RELATED APPLICATIONS

This application is the United States national stage filing of corresponding international application number PCT/US2006/013751 filed on Apr. 12, 2006, and claims priority to and benefit of PCT/US2006/013751, which is hereby incorporated by reference in its entirety.

FIELD OF INVENTION

The invention relates to the field of protein purification using surfactants.

BACKGROUND

Production of biological macromolecules, particularly proteins, often involves purity-enhancing steps based on physical and physicochemical properties. Difficulties encountered in such process steps include, but are not limited to, determining conditions which enable separation of soluble and insoluble molecules, relatively low recovery of the desired molecule after a treatment step, loss of biological activity in the course of the process, and sensitivity of the protein to process step conditions such as pH.

Surfactants have been utilized in the processing of biological macromolecules. Cationic surfactants are a recognized subclass of surfactants, and include amphipathic ammonium compounds. Amphipathic ammonium compounds comprise quaternary ammonium compounds of the general formula $QN^+$ and paraffin chain primary ammonium compounds of the general formula $RNH_3^+$. Both types of amphipathic ammonium compounds include long-chain ammonium surfactants that have a long aliphatic chain of preferably at least six carbon atoms (Scott (1960) Methods Biochem. Anal. 8:145-197, incorporated herein by reference in its entirety). The long-chain quaternary ammonium surfactants are known to interact with biological macromolecules. The long-chain quaternary ammonium compounds have at least one substituent at the nitrogen which consists of a linear alkyl chain with 6-20 carbon atoms. The best known representatives of this class are the benzalkonium salts (chlorides and bromides), hexadecylpyridinium chloride dequalinium acetate, cetyldimethylammonium bromide (CTAB) and hexadecylpyridinium chloride (CPCl), and benzethonium chloride. Quaternary ammonium surfactants include salts such as cetyl pyridinium salts, e.g. cetyl pyridinium chloride (CPC), stearamide-methylpyridinium salts, lauryl pyridinium salts, cetyl quinolynium salts, lauryl aminopropionic acid methyl ester salts, lauryl amino propionic acid metal salts, lauryl dimethyl betaine stearyl dimethyl betaine, lauryl dihydroxyethyl betaine and benzethonium salts. Alkyl pyridinium salts comprise stearyl-trimethyl ammonium salts, alkyl-dimethylbenzyl-ammonium chloride, and dichloro-benzyldimethyl-alkylammonium chloride.

Known uses of cationic surfactants for purifying biological macromolecules include 1) solubilization of aggregates, including protein aggregates; 2) elution of chromatographic column-bound biological macromolecules; and 3) precipitation of polyanions such as hyaluronic acid (HA), nucleic acids, and heparin (and molecules which co-precipitate with polyanions).

Cationic surfactants have been used for solubilizing protein aggregates. Otta and Bertini ((1975) Acta Physiol. Latinoam. 25:451-457, incorporated herein by reference in its entirety) demonstrated that active uricase could be solubilized from rodent liver peroxizomes with the quaternary ammonium surfactant, Hyamine 2389. It is found that increase of the ammonium surfactant concentration resulted in increase of dissolution of both uricase (based on enzymatic activity) and total protein such that there is no increase in the relative amount of uricase protein with respect to the amount of total protein. In other words, there was no selective solubilization of the uricase protein with respect to the total protein, and the uricase protein did not constitute a higher percentage of the total protein upon solubilization with the cationic surfactant. Thus, in this process, uricase purity with respect to the total protein content is apparently not enhanced as a result of quaternary ammonium surfactant solubilization.

In another study, Truscoe ((1967) Enzymologia 33:1 19-32, incorporated herein by reference in its entirety) examined a panel of cationic, anionic, and neutral detergents for their extraction efficacy of urate oxidase (uricase) from ox kidney powders. While the neutral and anionic detergents were found to enhance soluble urate oxidase activity, the cationic detergents, e.g., quaternary ammonium salts, were found to decrease total enzymatic activity with increasing concentration. The authors concluded that cationic detergents were not useful for purifying ox kidney urate oxidase Solubilization of recombinant proteins, porcine growth hormone, methionyl-porcine growth hormone, infectious bursal disease virus protein, B-galactosidase fusion protein, from E. coli inclusion bodies or cells, with cationic surfactants is described in U.S. Pat. No. 4,797,474, U.S. Pat. No. 4,992,531, U.S. Pat. No. 4,966,963, and U.S. Pat. No. 5,008,377, each incorporated herein by reference in its entirety. Solubilization under alkaline conditions is accomplished using quaternary ammonium compounds including cetyltrimethylammonium chloride, mixed n-alkyl dimethyl benzylammonium chloride, CPC, N,N-dimethyl-N-[2-[2-[4-(1,1,3,3,-tetramethylbutyl)-phenoxy]ethoxy]ethyl]benzenemethanammonium chloride, tetradecyl trimethylammonium bromide, dodecyl trimethylammonium bromide, cetyl trimethylammonium bromide. These publications mention that, after each solubilization process, the solutions are centrifuged, and little to no pellet is observed in each case. This observation suggests that most or all of the proteins are solubilized without regard to selectivity for the solubilization of a target protein. The purity of the recovered proteins is not indicated. U.S. Pat. No. 5,929,231, incorporated herein by reference in its entirety, describes cetyl pyridinium chloride (CPC) disintegration of granules and aggregates containing starches. Thus, the prior art relates to use of cationic surfactants for general, nonspecific solubilization of particulate biological macromolecules. These methods of the prior art do not disclose increasing the purity of a desired target protein with respect to total protein with a cationic surfactant.

Cationic surfactants have also been used to elute biological macromolecules adsorbed to cation exchange resins or aluminum-containing adjuvants (Antonopoulos, et al. (1961) Biochim. Biophys. Acta 54:213-226; Embery (1976) J. Biol. Buccale 4:229-236; and Rinella, et al. (1998) J. Colloid Interface Sci. 197:48-56, each of which is incorporated herein by reference in its entirety). U.S. Pat. No. 4,169,764, incorporated herein by reference in its entirety, describes elution of urokinase from carboxymethyl cellulose columns using a wide variety of cationic surfactant solutions. The authors state a preference for using tetra substituted ammonium salts in which one alkyl group is a higher alkyl group up to 20 carbon atoms and the others are lower alkyl groups up to 6 carbon atoms. Use of such cationic surfactants enables removal of biological macromolecules from their attachment to a solid matrix.

Conversely, impregnation of filters such as those composed of nylon, with cationic surfactant enables immobilizing of polysaccharides or nucleic acids (Maccari and Volpi (2002) Electrophoresis 23:3270-3277; Benitz, et al. (1990) U.S. Pat. No. 4,945,086; Macfarlane (1991) U.S. Pat. No. 5,010,183, each of which is incorporated herein by reference in its entirety). This phenomenon is apparently due to cationic surfactant-polyanion interactions which enable precipitation of the polyanion.

It is well established that amphipathic ammonium compounds, which comprise quaternary ammonium compounds of the general formula $QN^+$ and paraffin chain primary ammonium compounds of the general formula $RNH_3^+$, can precipitate polyanions under defined conditions (reviewed in Scott (1955) Biochim. Biophys. Acta 18:428-429; Scott (1960) Methods Biochem. Anal. 8:145-197; Laurent, et al., (1960) Biochim. Biophys. Acta 42:476-485; Scott (1961) Biochem. J. 81:418-424; Pearce and Mathieson (1967) Can. J. Biochemistry 45:1565-1576; Lee (1973) Fukushima J. Med. Sci. 19:33-39; Balazs, (1979) U.S. Pat. No. 4,141,973; Takemoto, et al., (1982) U.S. Pat. No. 4,312,979; Rosenberg (1981) U.S. Pat. No. 4,301,153; Takemoto, et al., (1984) U.S. Pat. No. 4,425,431; d'Hinterland, et al., (1984) U.S. Pat. No. 4,460,575; Kozma, et al. (2000) Mol. Cell. Biochem. 203:103-112, each of which is incorporated herein by reference in its entirety). This precipitation is dependent on the precipitating species having a high polyanion charge density and high molecular weight (Saito (1955) Kolloid-Z 143:66, incorporated herein by reference in its entirety). The presence of salts can interfere with or reverse cationic surfactant-induced precipitation of polyanions.

Additionally, polyanions can be differentially precipitated from solutions containing protein contaminants, under alkaline pH conditions. In such cases, proteins not chemically bound to the polyanions will remain in solution, while the polyanions and other molecules bound to the polyanions will precipitate. For example, precipitation of polyanions such as polysaccharides and nucleic acids is accompanied by co-precipitation of molecules such as proteoglycans and proteins interacting with the polyanions (Blumberg and Ogston (1958) Biochem. J. 68:183-188; Matsumura, et al., (1963) Biochim. Biophys. Acta 69: 574-576; Serafini-Fracassini, et al. (1967) Biochem. J. 105:569-575; Smith, et al. (1984) J. Biol. Chem. 259:11046-11051; Fuks and Vlodavsky (1994) U.S. Pat. No. 5,362,641; Hascall and Heinegard (1974) J. Biol. Chem. 249:4232-4241, 4242-4249, and 4250-4256; Heinegard and Hascall (1974) Arch. Biochem. Biophys. 165: 427-441; Moreno, et al. (1988) U.S. Pat. No. 4,753, 796; Lee, et al. (1992) J. Cell Biol. 116: 545-557; Varelas, et al. (1995) Arch. Biochem. Biophys. 321: 21-30, each of which is incorporated herein by reference in its entirety).

The isoelectric point (or pI) of a protein is the pH at which the protein has an equal number of positive and negative charges. Under solution conditions with pH values close to (especially below) a protein's isoelectric point, proteins can form stable salts with strongly acidic polyanions such as heparin. Under conditions which promote precipitation of such polyanions, the proteins complexed with the polyanions also precipitate (L B Jaques (1943) Biochem. J. 37:189-195; A S Jones (1953) Biochim. Biophys. Acta 10:607-612; J E Scott (1955) Chem and Ind 168-169; U.S. Pat. No. 3,931,399 (Bohn, et al., 1976) and U.S. Pat. No. 4,297,344 (Schwinn, et al., 1981), each of which is incorporated herein by reference in its entirety).

U.S. Pat. No. 4,421,650, U.S. Pat. No. 5,633,227, and Smith, et al. ((1984) J. Biol. Chem. 259:11046-11051, each of which is incorporated herein by reference in its entirety) describe purification of polyanions by sequential treatment with a cationic surfactant and ammonium sulfate (that enables dissociation of polyanion-cationic surfactant complexes) and subsequent separation using hydrophobic interactions chromatography. European patent publication EP055188, incorporated herein by reference in its entirety, describes cationic surfactant-enabled separation of RTX toxin from lipopolysaccharide. However, there is no mass balance in the amount of lipopolysaccharide that is quantified by endotoxin activity assays. Neutralization of endotoxin activity by strongly interacting cationic compounds has been demonstrated (Cooper J F (1990) J Parenter Sci Technol 44:13-5, incorporated herein by reference in its entirety). Thus, in EP055188, the lack of endotoxin activity in the precipitate following treatment with increasing amounts of cationic surfactant possibly results from neutralization of the activity by surfactant-lipopolysaccharide complex formation.

The above-mentioned methods require intermediary polyanions, solid supports or aggregates comprising proteins with selective solubility by a cationic surfactant for enabling purification of soluble proteins using cationic surfactant. Hence, the prior art does not provide a method of purifying a target protein by contacting the protein with a cationic surfactant in an amount effective to preferentially precipitate proteins other than the target protein, i.e., contaminating proteins, particularly when such contacting is done in the absence of intermediary polyanions, solid supports, or aggregates of proteins. Often, one skilled in the art encounters mixtures of soluble proteins and does not have a simple, efficient means for purifying the desired protein. The novel method for purifying proteins, described herein, enables efficient purification of target proteins by using cationic surfactants to preferentially precipitate proteins other than the target protein. Preferably such precipitation of contaminating proteins is direct, and does not depend upon the presence of polyanions, solid supports or aggregates comprising the contaminating proteins and other molecules.

SUMMARY OF THE INVENTION

The subject invention provides a method for purifying a target protein from a mixture comprising the target protein and contaminating protein, comprising the steps of exposing the mixture to an effective amount of a cationic surfactant such that the contaminating protein is preferentially precipitated and recovering the target protein.

The protein concentration (A) and enzymatic activity (B) of mammalian uricase, from dissolved E. coli inclusion bodies, are measured following the indicated CPC treatments and centrifugal separation. The specific activity (C) of each isolate is calculated as a ratio of these values (activity/protein concentration).

FIG. 2 depicts size-exclusion HPLC chromatographic analysis of crude mammalian uricase prepared from inclusion bodies and following treatment with 0.075% CPC.

Size-exclusion HPLC profiles of A. solubilized E. coli inclusion bodies without CPC treatment, and B. the supernatant following CPC (0.075%) precipitation and filtration are analyzed. The areas of each peak and the percent of total area are summarized in the adjacent tables.

Figure 3:
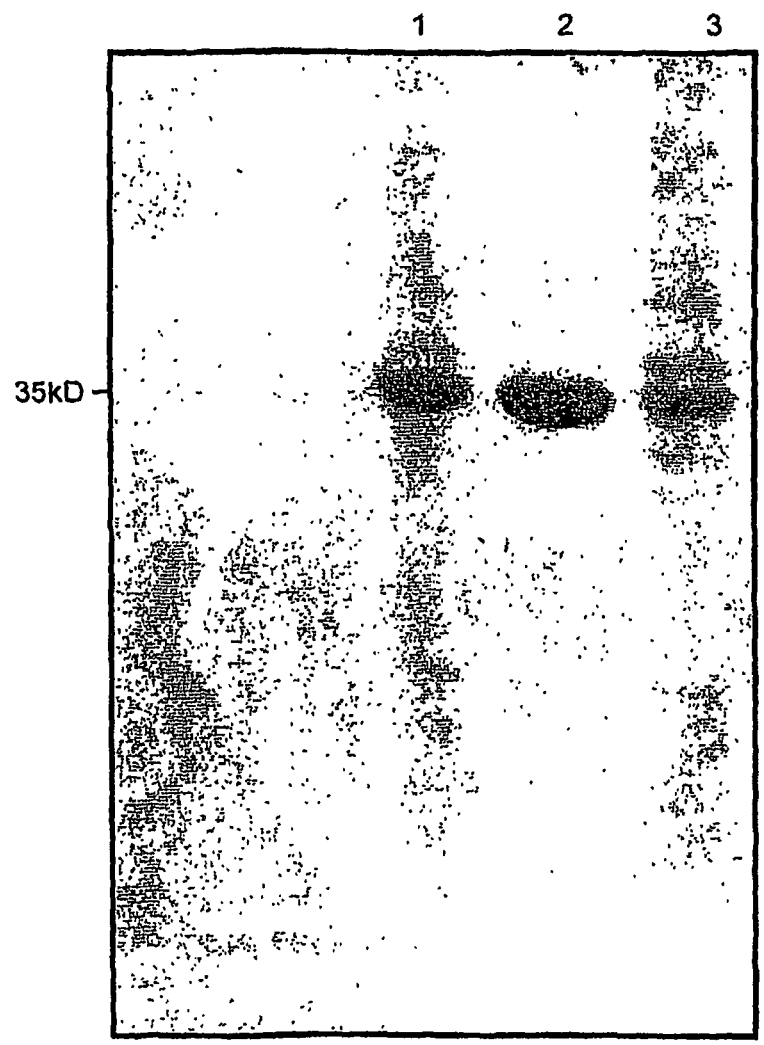

FIG. 3 depicts SDS-PAGE (15% gel) analysis of CPC treated uricase.

The uricase-containing samples are prepared as described in Example 1. Samples from various process steps are aliquoted as follows: Lane 1—dissolved IBs; Lane 2—supernatant after CPC treatment; Lane 3—pellet after CPC treatment.

Figure 4A:
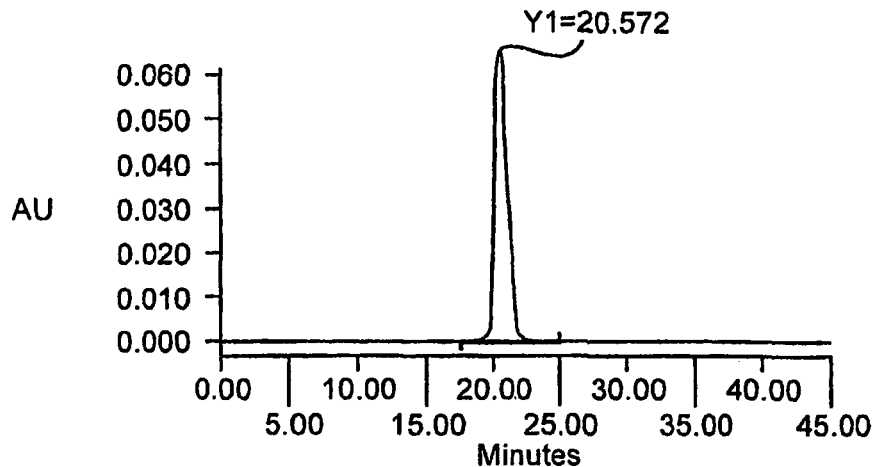

FIG. 4 depicts size-exclusion HPLC analysis of crude scFv antibody following treatment with 0.02% CPC.

Size-exclusion HPLC profiles of A. Reference standard BTG-271 scFv antibody, B. solubilized inclusion bodies, and C. the supernatant following refolding and CPC (0.02%) precipitation and filtration are analyzed. The areas of each peak and the percent of total area are summarized in the adjacent tables.

Figure 5:
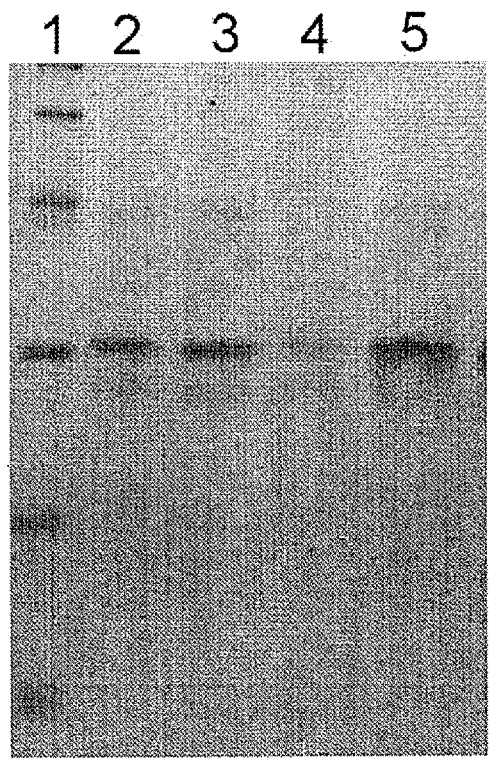

FIG. 5 depicts SDS-PAGE (15% gel) analysis of CPC treated scFv antibody.

The scFv antibody-containing samples from various process steps and standards are presented in the following order: Lane 1—molecular weight standards; Lane 2—dissolved IBs; Lane 3—refolded protein; Lane 4—CPC pellet; Lane 5—supernatant after CPC treatment.

Figure 6A:
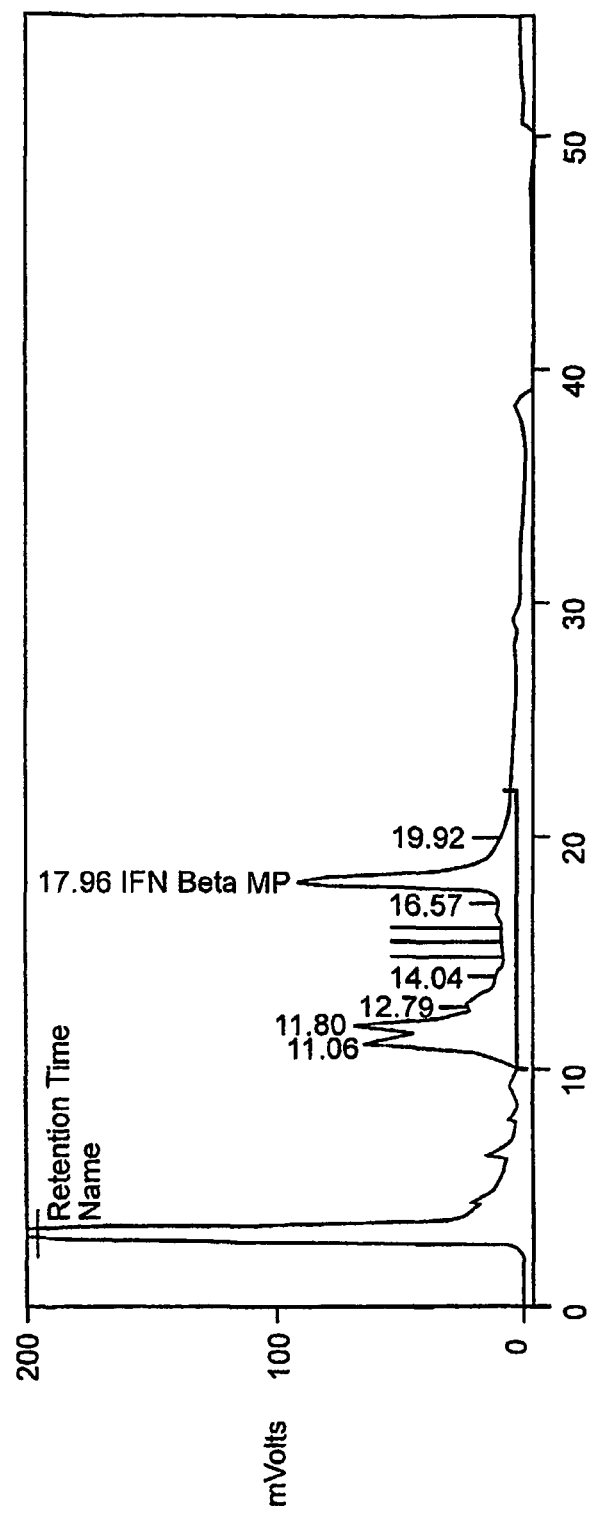
Figure 6B:
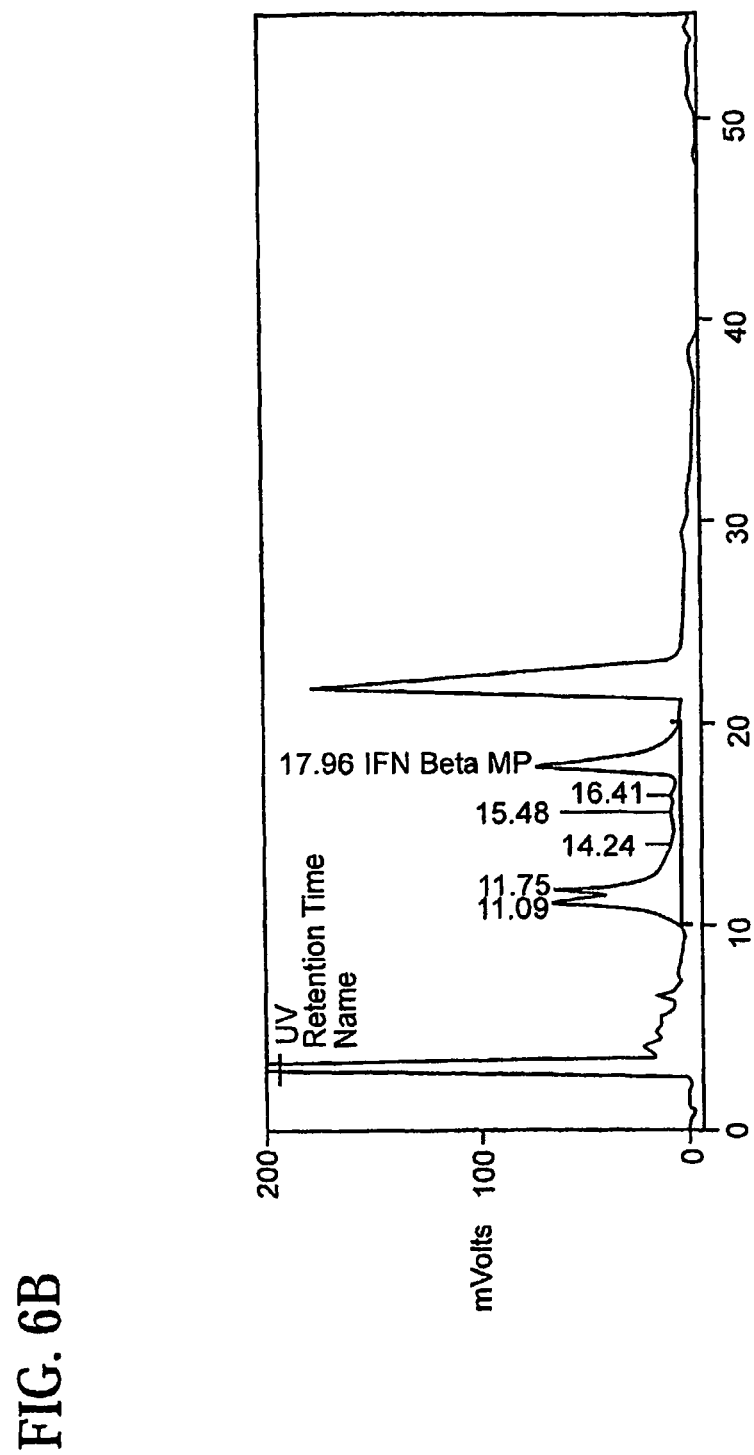

FIG. 6 depicts HPLC gel filtration chromatography of interferon beta before and after treatment with CPC.

A. Before CPC treatment
B. After CPC treatment.

200 μl of a solution of 0.1 mg/ml interferon beta was loaded into the column.

DETAILED DESCRIPTION OF THE INVENTION

Proteins are ampholytes, having both positive and negative charges. The pH of a solution and charged molecules that interact with a protein impact the net charge of that protein. Strong interactions between proteins can occur when the net charge of a protein is neutral (the isoelectric point). When the pH of the solution is below the isoelectric point of the protein, the protein has a net positive charge, and there may be electrostatic repulsion between cationic molecules, including other proteins.

It is an object of the invention to provide a method for purifying a solubilized target protein from a solution comprising a mixture of the target protein and contaminating proteins comprising contacting the solubilized mixture with an effective amount of a cationic surfactant and recovering the target protein. Cationic surfactants are surface-active molecules with a positive charge. In general, these compounds also have at least one non-polar aliphatic group. Preferably the target protein has an isoelectric point greater than 7. In a particular embodiment, the pH of the solution is about the same as the isoelectric point of the target protein. In a preferred embodiment, the pH of the solution is less than the isoelectric point of the target protein. In a particular embodiment, when the pH of the solution is above the isoelectric point of the target protein, the pH of the solution is within 1-2 pH units of the isoelectric point of the target protein. In a particular embodiment, when the pH of the solution is above the isoelectric point of the target protein, the pH of the solution is within 1 pH unit of the isoelectric point of the target protein.

In a particular embodiment, the contaminating protein or proteins are preferentially precipitated, thereby increasing the proportion of the proteins remaining in solution represented by the target protein. For example, starting from a solution of target protein and contaminating protein wherein the target protein is 20% of the total protein in solution, one can purify the target protein using the methods provided to achieve a solution wherein the target protein is 30% or more, 40% or more, 50% or more, 60% or more, 70% or more, 80% or more, 90% or more, 95% or more of the total protein remaining in solution.

As used herein, the term "preferentially precipitate" means that a protein or group of proteins are precipitated to a greater extent than another protein or group of proteins. For example, in the case of a mixture of a target protein and contaminating proteins, the contaminating proteins are preferentially precipitated with respect to the target protein when 20% or more of the contaminating proteins are precipitated, while less than 20% of the target protein is precipitated. Preferably, a high percentage of contaminating proteins are precipitated, while a low percentage of the target protein is precipitated. In preferred embodiments, 30% or more of the contaminating proteins are precipitated, while less than 30% of the target protein is precipitated; 40% or more of the contaminating proteins are precipitated, while less than 40% of the target protein is precipitated; 50% or more of the contaminating proteins are precipitated, while less than 50% of the target protein is precipitated; 60% or more of the contaminating proteins are precipitated, while less than 60% of the target protein is precipitated; 70% or more of the contaminating proteins are precipitated, while less than 70% of the target protein is precipitated; 80% or more of the contaminating proteins are precipitated, while less than 80% of the target protein is precipitated; 90% or more of the contaminating proteins are precipitated, while less than 90% of the target protein is precipitated; 95% or more of the contaminating proteins are precipitated, while less than 95% of the target protein is precipitated. Preferably, a small percentage of the target protein is precipitated. For example, less than 60%, less than 50%, less than 40%, less than 30%, less than 20%, less than 10%, less than 5% or less than 1% of the target protein is precipitated.

In a particular embodiment, the total amount of protein in solution (target protein plus contaminating protein), prior to carrying out the purification method of the invention, is from 0.1 to 10 mg/ml. In particular embodiments, the total amount of protein in solution prior to carrying out the purification method of the invention is from 0.1 to 3 mg/ml, 0.3 to 2 mg/ml, 0.5 to 2 mg/ml, 0.5 to 1 mg/ml, 1 to 2 mg/ml, or about 1 mg/ml.

In particular embodiments, the preferential precipitation of contaminating proteins is direct, and does not depend, or does not substantially depend, upon the presence of polyanions. In another embodiment, the preferential precipitation of contaminating proteins is direct, and does not depend, or does not substantially depend, upon the presence of a solid support. In another embodiment, the preferential precipitation of contaminating proteins does not depend, or does not substantially depend, upon the presence of aggregates between contaminating proteins and other molecules. The preferential precipitation of contaminating proteins does not depend or substantially depend upon a component (e.g., polyanions, solid supports, or aggregates of contaminating proteins and other molecules) when, for example, the removal of that component does not effect or does not substantially effect, respectively, the preferential precipitation of contaminating protein. An example of an insubstantial effect of the removal of a component would be that the contaminating proteins are preferentially precipitated both when the component is present and when it is absent. A further example would be the contaminating proteins are preferentially precipitated to the same extent when the component is present and when it is absent. Preferably, the same or substantially the same amount of contaminating proteins are precipitated in the absence or substantial absence of the component as is in the presence of the component.

In another embodiment, the method is performed in the absence of polyanions or in the absence of substantial amounts of polyanions. In another embodiment, the method is performed in the absence of a solid support or in the absence of a substantial solid support. In another embodiment, the method is performed in the absence of aggregates between contaminating proteins and other molecules, or in the absence of substantial amounts of aggregates between contaminating proteins and other molecules. Preferably, the method is performed in the absence of or in the absence of substantial amounts of two or three members of the group consisting of polyanions; a solid support; and aggregates between contaminating proteins and other molecules.

Once provided the method of the invention, it is routine for one of skill in the art to select the particular surfactant used and the conditions, e.g., pH, temperature, salinity, cationic surfactant concentration, total protein concentration, under which this procedure is accomplished to enhance efficiency of the purification of a particular target protein. For example, purifications performed at differing pH values and surfactant concentrations may be compared to establish the optimal purification conditions. Examples of this procedure are provided below in the Examples section. In a particular embodiment, the pH of the solution is chosen such that it is as high as is possible without substantially reducing the amount of target protein recovered.

It is a further objective of the invention to provide a method for determining conditions which enable efficient purification of target proteins on the basis of their solubility, as impacted by cationic surfactants.

An effective amount of cationic surfactant is an amount of surfactant that causes the preferential precipitation of contaminating proteins. In particular embodiments, the effective amount of surfactant precipitates 40%, 50%, 60%, 70%, 80%, 90%, 95% or 99% of the contaminating proteins.

In an embodiment of the invention, the cationic surfactant is added to a concentration of from 0.001% to 5.0%, preferably the cationic surfactant is added to a concentration of from 0.01% to 0.5% and more preferably, the cationic surfactant is added to a concentration of from 0.03% to 0.2%. In particular embodiments, the cationic surfactant is added to a concentration of from 0.01% to 0.1%, 0.01% to 0.075%, 0.01% to 0.05% or 0.01% to 0.03%.

In an embodiment of the invention, the above-mentioned method is accomplished when the cationic surfactant is an amphipathic ammonium compound.

In a preferred embodiment, the solubilized target protein is subjected to further processing after contaminating proteins have been preferentially precipitated. Such further processing can include additional purification steps, assays for activity or concentration, dialysis, chromatography (e.g., HPLC, size exclusion chromatography), electrophoresis, dialysis, etc.

As used herein, amphipathic ammonium compounds comprise compounds having both cationic and non-polar components with the general formula of either $QN^+$ or $RNH_3^+$. Q indicates that the nitrogen is a quaternary ammonium (covalently bonded to four organic groups which may or may not be bonded one to another). When organic groups are bonded one to another, they may form cyclic aliphatic or aromatic compounds, depending on the electronic configuration of the bonds between the components which form the cyclic structure. When the amphipathic ammonium compound selected has the general formula, $RNH_3^+$, the compound is a primary amine wherein R is an aliphatic group. Aliphatic groups are open chain organic groups.

In an embodiment of the invention, the selected amphipathic ammonium compound may form a salt with a halide. Commonly, halide salts refer to those comprising fluoride, chloride, bromide, and iodide ions.

In an embodiment of the invention, the amphipathic ammonium compound has at least one aliphatic chain having 6-20 carbon atoms, preferably, the amphipathic ammonium compound has at least one aliphatic chain having 8-18 carbon atoms.

In an embodiment of the invention, the selected amphipathic ammonium compound is selected from the group consisting of cetyl pyridinium salts, stearamide-methylpyridinium salts, lauryl pyridinium salts, cetyl quinolynium salts, lauryl aminopropionic acid methyl ester salts, lauryl amino propionic acid metal salts, lauryl dimethyl betaine, stearyl dimethyl betaine, lauryl dihydroxyethyl betaine and benzethonium salts.

Amphipathic ammonium compounds which may be used include, but are not limited to hexadecylpyridinium chloride dequalinium acetate, hexadecylpyridinium chloride, cetyltrimethylammonium chloride, mixed n-alkyl dimethyl benzylammonium chloride, cetyl pyridinium chloride (CPC), N,N-dimethyl-N-[2-[2-[4-(1,1,3,3,-tetramethylbutyl)-phenoxy]ethoxy]ethyl]benzenemethanammonium chloride, alkyl-dimethylbenzyl-ammonium chloride, and dichlorobenzyldimethyl-alkylammonium chloride, tetradecyl trimethylammonium bromide, dodecyl trimethylammonium bromide, cetyl trimethylammonium bromide, lauryl dimethyl betaine stearyl dimethyl betaine, and lauryl dihydroxyethyl betaine.

In an embodiment of the invention, the amphipathic ammonium compound is a cetylpyridinium salt such as cetylpyridinium chloride.

In an embodiment of the invention, the mixture containing the desired protein further comprises cellular components such as cellular components derived from microorganisms, for example, bacteria such as *E. coli*.

In an embodiment of the invention, the cellular components are one or more proteins.

In an embodiment of the invention the target protein may be a recombinant protein, for example, an enzyme.

The method of the invention can be used to purify a variety of proteins. These proteins may include, but are not limited to antibodies, uricase, interferon-beta, leech factor X inhibitor, acid deoxyribonuclease II, elastase, lysozyme, papain, peroxidase, pancreatic ribonuclease, trypsinogen, trypsin, cytochrome c, erabutoxin, *staphylococcus aureus* enterotoxin C1, and monoamine oxidase A, and other proteins that are positively charged under alkaline conditions.

In an embodiment of the invention the target protein may be an antibody, receptor, enzyme, transport protein, hormone, or fragment thereof or a conjugate e.g., conjugated to a second protein or a chemical or a toxin.

Antibodies include but are not limited to monoclonal, humanized, chimeric, single chain, bispecific, Fab fragments, F(ab')2 fragments, fragments produced by a Fab expression library, anti-idiotypic (anti-Id) antibodies, and epitope-binding fragments of any of the above, but with the proviso that at the conditions of the purification the antibody is positively charged.

For preparation of monoclonal antibodies, any technique that provides for the production of antibody molecules by continuous culture of cell lines may be used. These include but are not limited to the hybridoma technique of Kohler and Milstein, (1975, Nature 256, 495-497; and U.S. Pat. No. 4,376,110), the human B-cell hybridoma technique (Kozbor et al., 1983, Immunology Today 4, 72; Cole et al., 1983, Proc. Natl. Acad. Sci. USA 80, 2026-2030), and the EBV-hybridoma technique to produce human monoclonal antibodies (Cole et al., 1985, Monoclonal Antibodies And Cancer Therapy, Alan R. Liss, Inc., pp. 77-96).

Such antibodies may be used as the basis from which to clone and thus recombinantly express individual heavy and light chains. The two chains may be recombinantly expressed in the same cell or combined in vitro after separate expression and purification. Nucleic acids (e.g., on a plasmid vector) encoding a desired heavy or light chain or encoding a molecule comprising a desired heavy or light chain variable domain can be transfected into a cell expressing a distinct antibody heavy or light chain or molecule comprising an antibody heavy or light chain, for expression of a multimeric protein. Alternatively, heavy chains or molecules comprising the variable region thereof or a CDR thereof can optionally be expressed and used without the presence of a complementary light chain or light chain variable region. In other embodiments, such antibodies and proteins can be N or C-terminal modified, e.g., by C-terminal amidation or N-terminal acetylation.

A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 5,816,397.) Techniques for the production of chimeric antibodies include the splicing the genes from a mouse antibody molecule of appropriate antigen specificity together with genes from a human antibody molecule of appropriate biological activity (see for example, Morrison, et al., 1984, Proc. Natl. Acad. Sci., 81, 6851-6855; Neuberger, et al., 1984, Nature 312, 604-608; Takeda, et al., 1985, Nature 314, 452-454).

Humanized antibodies are antibody molecules from non-human species having one or more complementarity-determining regions (CDRs) from the non-human species and framework regions from a human immunoglobulin molecule. Techniques for the production of humanized antibodies are described for example in Queen, U.S. Pat. No. 5,585,089 and Winter, U.S. Pat. No. 5,225,539. The extent of the framework regions and CDRs have been precisely defined (see, "Sequences of Proteins of Immunological Interest", Kabat, E. et al., U.S. Department of Health and Human Services (1983).

Single chain antibodies are formed by linking the heavy and light chain fragments of the Fv region via an amino acid bridge, resulting in a single chain polypeptide. Techniques for the production of single chain antibodies are described for example in U.S. Pat. No. 4,946,778; Bird, 1988, Science 242, 423-426; Huston, et al., 1988, Proc. Natl. Acad. Sci. USA 85, 5879-5883; and Ward, et al., 1989, Nature 334, 544-546).

A bispecific antibody is a genetically engineered antibody which recognizes two types of targets e.g. (1) a specific epitope and (2) a "trigger" molecule e.g. Fc receptors on myeloid cells. Such bispecific antibodies can be prepared either by chemical conjugation, hybridoma, or recombinant molecular biology techniques.

Antibody fragments include but are not limited to: The F(ab')2 fragments, which can be produced by pepsin digestion of the antibody molecule and the F(ab') fragments, which can be generated by reducing the disulfide bridges of the F(ab')2 fragments. Alternatively, Fab expression libraries may be constructed (Huse, et al., 1989, Science 246, 1275-1281) to allow rapid and easy identification of monoclonal Fab fragments with the desired specificity.

In an embodiment of the invention, the protein is uricase.

In another embodiment of the invention, the uricase is a mammalian uricase.

In another embodiment of the invention, the mammalian uricase is a variant mammalian uricase.

In another embodiment of the invention, the mammalian uricase is a porcine uricase.

In another embodiment of the invention, the variant porcine uricase is designated PKS$\Delta$N uricase.

In another embodiment of the invention, the protein is an antibody.

In another embodiment of the invention, the antibody is a single chain antibody.

In another embodiment of the invention, the protein is an interferon.

In another embodiment of the invention the interferon is interferon beta. In a particular embodiment, the interferon is interferon beta 1b. Nagola, S. et al., Nature, 284:316 (1980); Goeddel, D. V. et al., Nature, 287:411 (1980); Yelverton, E. et al., Nuc. Acid Res., 9:731 (1981); Streuli, M. et al., Proc. Nat'l Acad. Sci. (U.S.), 78:2848 (1981); European Pat. Application No. 28033, published May 6, 1981; 321134, published Jul. 15, 1981; 34307 published Aug. 26, 1981; and Belgian Patent No. 837379, issued Jul. 1, 1981 described various methods for the production of beta-interferon employing recombinant DNA techniques. Procedures for recovering and purifying bacterially produced IFNs are described in U.S. Pat. Nos. 4,450,103; 4,315,852; 4,343,735; and U.S. Pat. No. 4,343,736; and Derynck et al., Nature (1980) 287:193-197 and Scandella and Kornberg, Biochemistry, 10:4447 (1971).

In a particular embodiment, the target protein is leech factor Xa. Leech factor Xa may be produced by any method known to one of skill in the art, such as the method described in U.S. Pat. No. 6,211,341 and International Patent Publication No. WO94/23735.

In an embodiment of the invention, the contacting is done for between about 1 minute and about 48 hours, more preferably from about 10 minutes to about 24 hours, about 30 minutes to about 12 hours, about 30 minutes to about 8 hours, about 30 minutes to about 6 hours, about 30 minutes to about 4 hours, about 30 minutes to about 2 hours, about 30 minutes to about 1 hour, or about 1 to about 2 hours.

In an embodiment of the invention, the contacting is done at a temperature from about 4° C. to about 36° C.; more preferably from about 4° C. to about 26° C.

The subject invention also provides use of cationic surfactant as a single agent for purifying a protein having an isoelectric point greater than 7 under alkaline conditions.

The subject invention also provides a uricase purified under alkaline conditions from a mixture by the addition of cetylpyridinium chloride to the mixture.

In an embodiment of the invention, the uricase is obtained from a bacterial cell comprising DNA encoding the uricase by a method comprising treating the bacterial cell so as to express the DNA and produce the uricase and recovering the uricase.

In an embodiment of the invention, the uricase is recovered from precipitates within the bacterial cell.

The subject invention also provides purified uricase for use in preparing a uricase-polymer conjugate.

The invention also provides a purified protein having an isoelectric point greater than 7 obtainable by a method comprising contacting a mixture containing the protein with an effective amount of a cationic surfactant under conditions such that the protein is positively charged or has an area of positive charge, and recovering the protein.

The subject invention also provides use of a cetylpyridinium salt for purifying a protein having an isoelectric point greater than 7.

As to the pH, in embodiments where the mixture is contacted with an effective amount of a cationic surfactant under conditions such that the target protein is positively charged, the pH will vary with the nature of the target protein. However, the pH is preferably between pH7 and pH11; preferred ranges are from about pH7 and pH10, pH7 to pH9, pH8 to pH11, pH8 to pH10 or pH8 to pH9.

EXAMPLES

The examples which follow are set forth to aid in understanding the invention but are not intended to and should not be construed to limit its scope in any way.

Example 1

Use of CPC for Purification of Recombinant Mammalian Uricase 1.1. Background

Pharmaceutical grade uricase must be essentially free of non-uricase protein. Mammalian uricase (isoelectric point of 8.67) produced in *E. coli* accumulated intracellularly in precipitates similar to organelles referred to as inclusion bodies (IBs) which can be easily isolated for further purification. In contrast to the classical view that IBs contain scrambled/mis-folded expressed protein, these IB-like elements contain correctly folded uricase in a precipitated form. Exposure of uricase IB-like elements to an alkaline pH, e.g., about pH 9-11, re-dissolved the precipitated protein. The uricase content in solubilized IB-like elements was about 40-60% and required extensive purification to obtain a homogeneous uricase preparation. Herein, we demonstrate purification of uricase and other protein with CPC that can be assessed by a variety of methods. For example, mammalian uricase purity can be assessed by determining the specific activity, the number of bands which appear following electrophoresis and staining of SDS-PAGE gels, and the number and size of peaks which appear in a chromatogram following size exclusion HPLC.

1.2. Materials and Methods 1.2.1. 50 mM NaHCO$_3$ Buffer (pH 10.3)

This buffer was prepared by dissolving NaHCO$_3$ to a final concentration of 50 mM. The pH was adjusted to 10.2-10.4. Depending on starting pH, 0.1 M HCl or 1 N NaOH may be used.

1.2.2. 10% CPC Solution

10% CPC was prepared by dissolving CPC in distilled water to a final concentration of 10 gr/100 ml.

1.2.3. Recombinant Porcine Uricase Expression

Recombinant mammalian uricase (urate oxidase) was expressed in *E. coli* K-12 strain W3110 F$^-$, as described in International Patent Publication WO00/08196 of Duke University and U.S. Patent Provisional Application No. 60/095,489, incorporated herein by reference in their entireties.

1.2.4. Culture and Harvest of Uricase-Producing Bacteria

Bacteria were cultured at 37° C. in growth medium containing casein hydrolysate, yeast extract, salts, glucose, and ammonia.

Following culture, bacteria in which uricase accumulated were harvested by centrifugation and washed with water to remove residual culture medium.

1.2.5. Cell Disruption and Recovery

Harvested cell pellet was suspended in 50 mM Tris buffer, pH 8.0 and 10 mM EDTA and brought to a final volume of approximately 20 times the dry cell weight (DCW). Lysozyme, at a concentration of 2000-3000 units/ml, was added to the suspended pellet while mixing, and incubated for 16-20 hours, at 4-8° C.

The cell lysate was treated by high shear mixing and subsequently by sonication. The suspension was diluted with an equal volume of deionized water and centrifuged. The pellet, containing uricase inclusion bodies, was diluted with deionized water (w/w) and centrifuged to further remove impurities. The pellet obtained from this last wash step was saved for further processing, and the supernatant was discarded.

1.2.6. Dissolution

The inclusion body (IB) pellet was suspended in 50 mM NaHCO$_3$ buffer, pH 10.3±0.1. The suspension was incubated at a temperature of 25±2° C. for about 0.5-2 hours to allow solubilization of the IB-derived uricase.

1.2.7. CPC Treatment

10% CPC solution was added in aliquots to homogenized IBs (pH 10.3), while briskly mixing, to obtain the desired CPC concentration. The sample was incubated for 1 to 24 hours as indicated, during which precipitating flakes formed. The sample was centrifuged for 15 minutes, at 12,000×g. The pellet and supernatant were separated, and the pellet was suspended with 50 mM NaHCO$_3$ buffer (pH 10.3) to the original volume. The enzymatic activity of each fraction was determined, and the fractions were concentrated and dialyzed to remove the remaining CPC.

1.2.8. Protein Assay

The protein content of aliquots of treated and untreated IB samples was determined using the modified Bradford method (Macart and Gerbaut (1982) Clin Chim Acta 122: 93-101).

1.2.9. Uricase Assay 1.2.9.1. Enzymatic activity

Activity of uricase was measured by the UV method (Fridovich, I. (1965) The competitive inhibition of uricase by oxonate and by related derivatives of s-triazines. J Biol Chem, 240, 2491-2494; modified by incorporation of 1 mg/ml BSA). Enzymatic reaction rate was determined, in duplicate samples, by measuring the decrease in absorbance at 292 nm resulting from the oxidation of uric acid to allantoin. One activity unit is defined as the quantity of uricase required to oxidize one μmole of uric acid per minute, at 25° C., at the specified conditions. Uricase potency is expressed in activity units per mg protein (U/mg).

The extinction coefficient of 1 mM uric acid at 292 nm in a 1 cm path length is 12.2. Therefore, oxidation of 1 μmole of uric acid per ml reaction mixture results in a decrease in absorbance of 12.2 mA$_{292}$. The absorbance change with time (ΔA$_{292}$ per minute) was derived from the linear portion of the curve. Uricase activity was then calculated as follows:

$$\text{Activity } (U/\text{ml}) = \frac{\Delta A_{292\,nm}(AU/\text{min}) \times DF \times V_{RM}}{V_S \times 12.2}$$

Where: $DF$ = Dilution factor;

$V_{RM}$=Total volume of reaction mixture (in μl)
$V_S$=Volume of diluted sample used in reaction mixture (in μl)

1.2.9.2. HPLC Analysis with Superdex 200

The amount and the relative percentage of the native uricase enzyme, as well as possible contaminants, were quantified according to the elution profile obtained by HPLC using a Superdex 200 column. Duplicate samples of uricase solution were injected into the column. The areas of each peak and the percent of total area were automatically calculated and summarized in the adjacent tables.

1.2.10. SDS-PAGE Analysis

Proteins in samples containing ~20 μg protein/lane, were separated on 15% SDS-PAGE gels. The resulting gels were stained with Coomassie brilliant blue.

1.3. Results

Figure 1A:
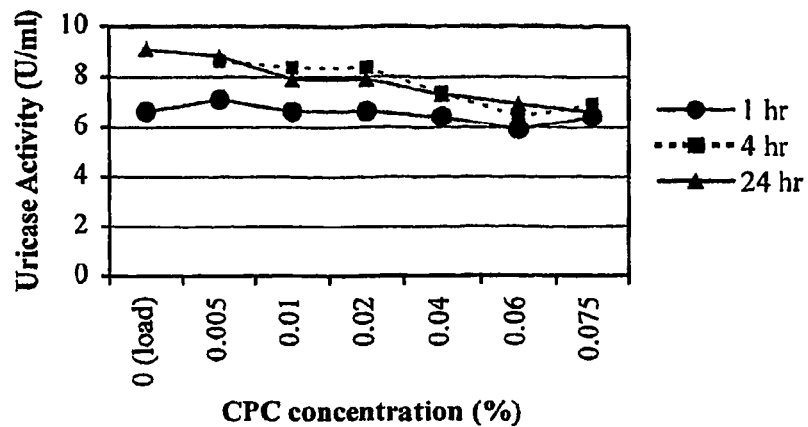
FIG. 1 depicts the effects of CPC concentration on uricase activity and purity.
Figure 1B:
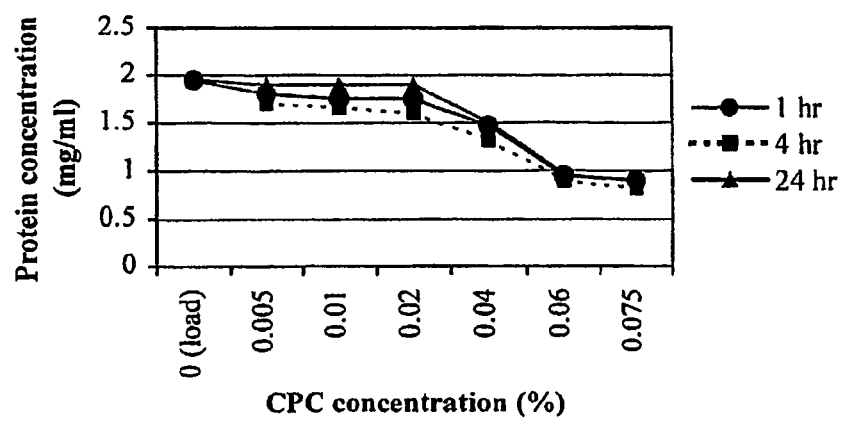
Figure 1C:
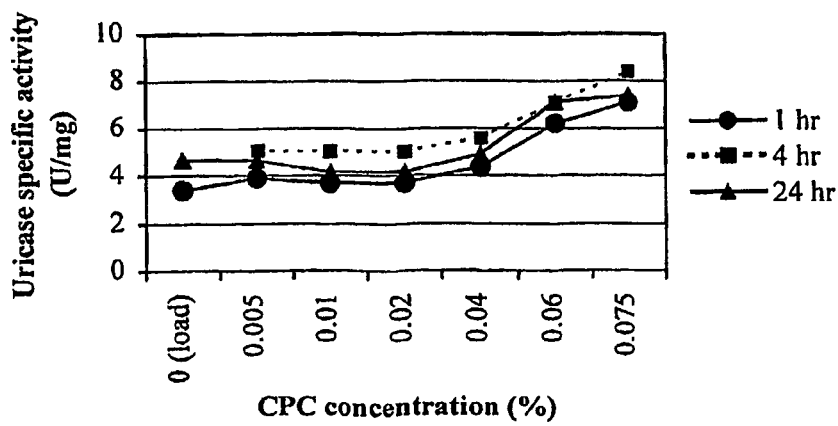

The effects of CPC (0.005-0.075%) treatment (for 1-24 hours) on uricase activity recovered in the supernatant, and its purity are presented in Table 1 and FIG. 1. Prior to CPC treatment (at pH 10.3), the protein concentration was 1.95 mg/ml, and the specific enzymatic activity was 3.4-4.67 U/mg. The results presented in FIG. 1B indicate that within each incubation period, the protein concentration of the supernatant decreased with increasing CPC concentration. At less than 0.04% CPC, a relatively minor effect on the protein concentration was observed. CPC, in concentrations of 0.04% to 0.075%, could reduce the protein concentration to about 50% of the original concentration.

In contrast to the effects of CPC on total protein concentration, the total soluble uricase activity was not significantly influenced by increasing CPC concentration and incubation time (FIG. 1A). Within each incubation period, the specific enzymatic activity (FIG. 1C) consistently increased as a function of CPC concentration within the range 0.04%-0.075%. This increase was a result of specific removal of non-uricase proteins. Since the specific enzymatic activity of the final purified enzyme was approximately 9 U/mg, the majority of contaminating proteins were removed by CPC precipitation. Indeed, HPLC and SDS-PAGE analyses performed support this conclusion.

1.4. Confirmation of CPC Enhancement of Uricase Purity

Uricase-containing IBs were isolated and solubilized, as described in section 1.3. Samples of the soluble material were analyzed prior to CPC treatment and following filtration of the CPC-precipitated protein.

Figure 2A:
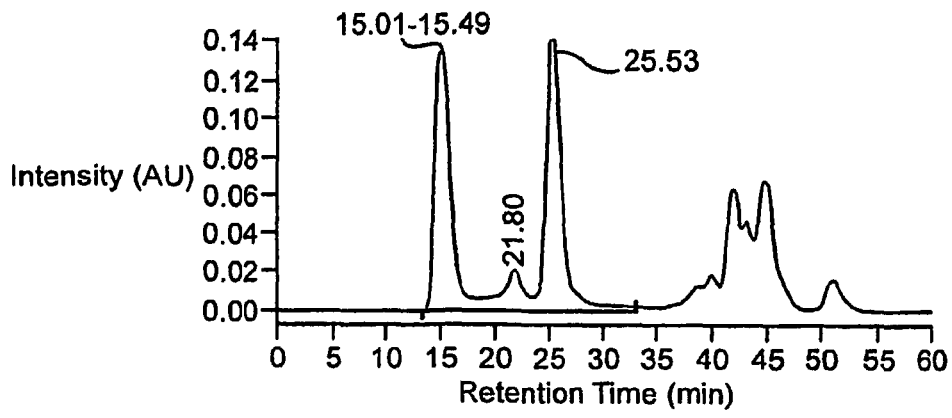
Figure 2B:
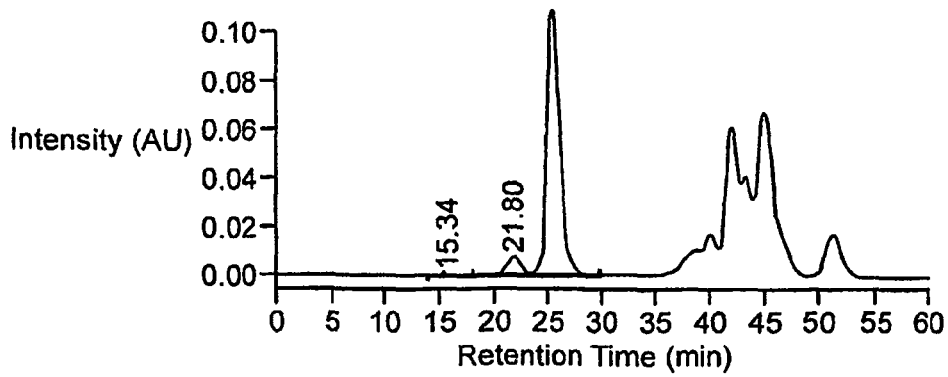

1.4.1. HPLC Analysis of Non-Uricase Proteins Following Treatment with 0.075% CPC HPLC analysis of solubilized IBs indicated that the uricase-associated peak (retention time (RT)~25.5 minutes) comprises about 46% of the protein of the crude IB sample (FIG. 2A). Following CPC treatment, the uricase-associated peak increased to approximately 92% of the protein (FIG. 2B), and was accompanied by significant reduction of the contaminants eluting between RT 15-22 min. (FIG. 2A). The area of the uricase peak is approximately 70% of that in FIG. 2A. Thus, these results indicate a doubling of uricase purity resulting from removal of non-uricase protein upon CPC treatment.

1.4.2. Effect of 0.075% CPC on Enzymatic Activity

The results (presented in Table 2) indicate that mass balance of uricase activity was retained during the treatment process. CPC exposure was found to precipitate 60% of all proteins in solution. More than 85% of the enzymatic activity remained in solution, thus the removal of extraneous protein afforded an increase in specific activity of the produced supernatant of more than 110%. As in most purification processes, some of the desired activity remained in the pellet. In this instance, only 17.6% of the original activity remained in the pellet (and was extracted using 50 mM sodium bicarbonate (7 mSi, pH 10.3) for analytical purposes), which is a relatively minor fraction of the total amount.

TABLE 1

EFFECT OF CPC EXPOSURE ON URICASE SPECIFIC ACTIVITY AND PURITY

| Incubation time (hr) | [CPC] (%) | Uricase activity (U/ml) | [Protein] (mg/ml) | Uricase specific activity (U/mg) |
|---|---|---|---|---|
| 1 | 0 (load) | 6.63 | 1.95 | 3.4 |
| 1 | 0.005 | 7.1 | 1.8 | 3.9 |
| 1 | 0.01 | 6.63 | 1.75 | 3.7 |
| 1 | 0.02 | 6.63 | 1.75 | 3.7 |
| 1 | 0.04 | 6.4 | 1.47 | 4.35 |
| 1 | 0.06 | 5.9 | 0.95 | 6.2 |
| 1 | 0.075 | 6.4 | 0.9 | 7.1 |
| 4 | 0.005 | 8.61 | 1.7 | 5.06 |
| 4 | 0.01 | 8.36 | 1.66 | 5.04 |
| 4 | 0.02 | 8.36 | 1.6 | 5.04 |
| 4 | 0.04 | 7.38 | 1.32 | 5.59 |
| 4 | 0.06 | 6.4 | 0.9 | 7.1 |
| 4 | 0.075 | 6.9 | 0.82 | 8.4 |
| 24 | 0.005 | 8.8 | 1.9 | 4.66 |
| 24 | 0.01 | 7.9 | 1.9 | 4.14 |
| 24 | 0.02 | 7.9 | 1.9 | 4.14 |
| 24 | 0.04 | 7.3 | 1.5 | 4.9 |
| 24 | 0.06 | 6.9 | 0.97 | 7.1 |
| 24 | 0.075 | 6.6 | 0.9 | 7.4 |
| 24 | 0 (load) | 9.1 | 1.95 | 4.67 |

TABLE 2

EFFECT OF CPC TREATMENT ON URICASE ACTIVITY

| Sample | Total activity (U) | Activity (U/ml) | [Protein] (mg/ml) | Specific activity (U/mg) | Activity recovered (%) |
|---|---|---|---|---|---|
| Before CPC | 490 | 4.9 | 2 | 2.46 | 100 |
| After CPC treatment | 418 | 4.18 | 0.8 | 5.2 | 85.3 |
| Pellet after CPC treatment | 86 | 0.8 | — | — | 17.6 |

1.4.3. SDS-PAGE Analysis Following Treatment with 0.075% CPC

Samples of the crude uricase, prior to exposure to CPC, and of the subsequent fractions, following separation of soluble and insoluble material, following CPC treatment, centrifugal separation of the fractions, and reconstitution of the pellet obtained after centrifugation, containing equal amounts of protein were analyzed by SDS-PAGE methodology. The results (see FIG. 3) show the presence of contaminating proteins prior to CPC treatment. Following CPC treatment, the pellet contained most of the contaminating proteins, while the supernatant contained uricase that resulted in the single major protein band.

Example 2

Effect of CPC on Purification of Single Chain (scFv) Antibodies 2.1. Materials and Methods
2.1.1. Buffers
2.1.1.1. Inclusion Body Dissolution Buffer
Dissolution buffer contained 6 M urea, 50 mM Tris, 1 mM EDTA, and 0.1 M cysteine. The pH of the buffer was titrated to 8.5.
2.1.1.2. Folding Buffer
Folding buffer contained 1 M urea, 0.25 mM NaCl, 1 mM EDTA, and 0.1 M cysteine. The pH of the buffer was titrated to 10.0.
2.1.2. Expression of scFv Antibodies in Bacteria
ScFv antibodies (pI 8.9) were expressed in *E. coli* transformed with a vector encoding a scFv having cysteine-lysine-alanine-lysine at the carboxyl end as described in PCT Publication WO 02/059264, incorporated herein by reference in its entirety.
2.1.3. Culture and Harvest of scFv Antibody-Producing Bacteria
ScFv-containing bacterial cells were cultured in minimal medium, at pH 7.2, and supplemented with L-arginine, final concentration 0.5%, during the five hour period prior to induction. Expression of scFv was induced by limitation of glucose amount in the medium. ScFv-containing bacterial cells were harvested from culture by ultra filtration.
2.1.4. Cell Disruption and Recovery of Inclusion Bodies
Harvested cell pellet was suspended in 50 mM Tris buffer, pH 8.0 and 10 mM EDTA and brought to a final volume of approximately 20 times the dry cell weight (DCW). Lysozyme, at a concentration of 2000-3000 units/ml, was added to the suspended pellet while mixing, then incubated for 16-20 hours, at 4° C.
The cell lysate was then treated by high shear mixing and subsequently by sonication. The scFv antibody-containing inclusion bodies were recovered by centrifugation at 10,000×g. The pellet was diluted approximately sixteen fold with deionized water (w/w) and centrifuged to further remove impurities. The pellet obtained from this last wash step was saved for further processing.
2.1.5. Dissolution and Refolding
The IB-enriched pellet was suspended in inclusion body dissolution buffer (see above), incubated for 5 hours at room temperature, and refolded in vitro in a solution based on arginine/oxidized glutathione. After refolding, the protein was dialyzed and concentrated by tangential flow filtration against containing urea/phosphate buffer.
2.1.6. CPC Treatment
10% CPC solution was added to the scFv refolding mixture to a final concentration of 0.02%, and after 1-2 hr incubation, at room temperature, the precipitate was removed by filtration. The supernatant contained the scFv antibody.
2.2. Results
2.2.1. Effect of CPC Concentration on Recoverable scFv Antibody The effects of CPC (at pH 7.5 or 10) on scFv antibody purity and recovery are presented in Table 3. Prior to CPC treatment, the initial amount of IB protein was 73 mg, containing 15.87 mg scFv antibody as determined by HPLC analysis on Superdex 75. The retention time (RT) of the scFv antibody-containing peaks was approximately 20.6 minutes. The results indicate that recovery of total protein generally decreased with increasing CPC concentration, and recovery of scFv antibody remained >80% when the CPC concentration was <0.03%. More efficient removal of contaminating protein was achieved at pH 7.5 relative to that at pH 10. Thus, scFv antibody purification was achieved by treatment with 0.01 to 0.03% CPC.

TABLE 3

Effect of CPC treatment on scFv antibody recovery and purity

| Treatment of soluble IBs | Total protein (mg) | Total scFv by HPLC (mg) | Purification factor | % recovery of scFv by HPLC |
|---|---|---|---|---|
| Control (before CPC) | 73 | 15.87 | | 100 |
| 0.01% CPC (pH 10) | 64 | 15.66 | 1.13 | 98.68 |
| 0.01% CPC (pH 7.5) | 50.76 | 14.97 | 1.36 | 94.33 |
| 0.015% CPC (pH 10) | 54 | 14.49 | 1.23 | 91.30 |
| 0.015% CPC (pH 7.5) | 39.96 | 14.22 | 1.64 | 89.60 |
| 0.02% CPC (pH 10) | 43 | 13.35 | 1.43 | 84.12 |
| 0.02% CPC (pH 7.5) | 37.8 | 13.02 | 1.58 | 82.04 |
| 0.03% CPC (pH 10) | 35 | 11.12 | 1.46 | 70.07 |
| 0.03% CPC (pH 7.5) | 37.8 | 12.47 | 1.52 | 78.58 |

Figure 4B:
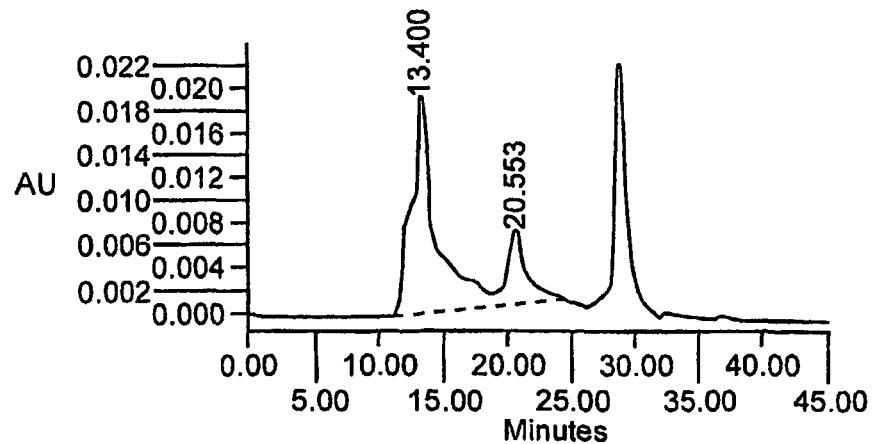
Figure 4C:
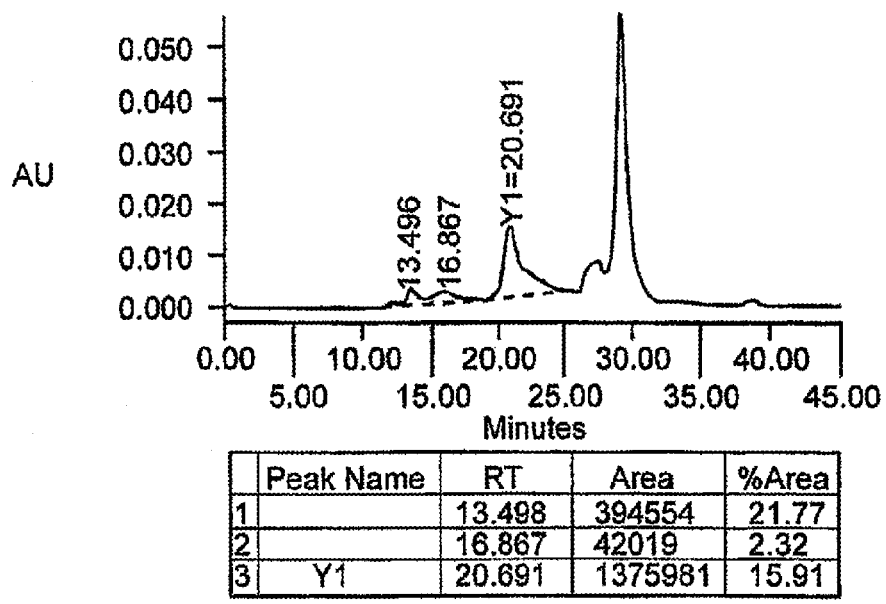

2.3. Confirmation of CPC Enhancment of scFv Antibody Purity
2.3.1. HPLC Analysis of scFv Recovery Following Treatment with CPC
HPLC analysis of refolded protein indicates that the scFv antibody-associated peak (retention time (RT)~20.6 minutes) comprised about 22.7% of the protein of the total protein (FIG. 4B). The chromatogram of FIG. 4C indicates that following treatment with 0.02% CPC, the scFv antibody-associated peak of the supernatant comprised approximately 75.9% of the total protein injected, a 3.3-fold purification. Thus, CPC treatment removed protein impurities from scFv antibody solutions.
2.3.2. SDS-PAGE Analysis on scFv Recovery Following Treatment with CPC
The results (see FIG. 5) indicate that prior to CPC treatment, the sample contained significant amounts of a large number of proteins. Similarly, following CPC treatment, the pellet contained a large number of proteins. In contrast, the post-CPC treatment supernatant contained one major protein band, that of scFv antibody.

Example 3

Effect of CPC on Purification of Recombinant Interferon-Beta

Interferon beta (IFN-beta, pI 8.5-8.9) was expressed in *E-coli* by known methods. Nagola, S. et al., Nature, 284:316 (1980); Goeddel, D. V. et al., Nature, 287:411 (1980);

Yelverton, E. et al., Nuc. Acid Res., 9:731 (1981); Streuli, M. et al., Proc. Nat'l Acad. Sci. (U.S.), 78:2848 (1981); European Pat. Application No. 28033, published May 6, 1981; 321134, published Jul. 15, 1981; 34307 published Aug. 26, 1981; and Belgian Patent No. 837379, issued Jul. 1, 1981 described various methods for the production of beta-interferon employing recombinant DNA techniques. Procedures for recovering and purifying bacterially produced IFNs are described in U.S. Pat. Nos. 4,450,103; 4,315,852; 4,343,735; and U.S. Pat. No. 4,343,736; and Derynck et al., Nature (1980) 287:193-197 and Scandella and Kornberg, Biochemistry, 10:4447 (1971). Inclusion bodies containing IFN-beta were isolated and solubilized.

The resulting solution was treated with CPC. The results shown in FIG. 6 indicate a substantial decrease in the level of contaminating proteins present after CPC treatment. The actual amount of IFN-beta (area under the peak) did not change appreciably following CPC treatment.

Table 4 summarizes the effects of the CPC treatment. Total protein (Bradford) decreased by 40%, UV absorbance decreased by about 40% but the amount of IFN-beta remained unchanged.

TABLE 4

| Sample and Treatment | Protein (mg/ml) | O.D $A_{280}$ | IFNb content (mg/ml)[a] | SEC Profile |
|---|---|---|---|---|
| Control (post protein folding no CPC, 1049-31) | 0.51 | 1.55 | 0.069 | Peak of R.T. 13[b] min is 15% of total area |
| Test (post protein folding and treatment with 0.05%CPC, 1049-31) | 0.3 | 1.0 | 0.069 | Peak of R.T. 13[b] min is 7.34% of total area |

[a] Quantified by Vydac C4 column
[b] The SEC profile contained several peaks. The peak eluting at 13 min (R.T. 13 min) is reduced upon treatment with CPC and corresponds to the region where high molecular weight proteins and variants thereof elute.

Example 4

Effect of CPC on Purification of Factor Xa Inhibitor

CPC was used to purify leech factor Xa inhibitor. Leech factor Xa inhibitor (FXaI, pI 8.4-9.1) may be produced as described in U.S. Pat. No. 6,211,341 and International Patent Publication No. WO94/23735. Following isolation of FXaI-containing inclusion bodies (IBs), the FXaI was purified from IBs substantially as described in example 1. After dissolution of the IB pellet, the preparation was incubated with 10% CPC solution. Then, the mixture was centrifuged for 15 minutes, at 12,000×g. The pellet and supernatant were separated. The pellet was suspended with 50 mM NaHCO$_3$ buffer to the original volume. The pellet and supernatant were separately concentrated and dialyzed to remove the remaining CPC. The protein content and activity were assayed and FXaI was found to be the predominant component in the supernatant and substantially absent from the pellet. The results indicate that CPC treatment enhanced the efficiency of recovery and the purity of the recovered FXaI.

Example 5

Purification of Carboxypeptidase B (CPB) by CPC

Identical amounts of inclusion bodies obtained from a clone expressing CPB were solubilized in 8 M urea, pH 9.5 (control and test). Production of CPB is described in International Patent Publication No. WO96/23064 and in U.S. Pat. No. 5,948,668. The test sample was treated with CPC 0.11% and clarified by filtration prior to refolding. Refolding of control and test samples were carried out by diluting the solutions 1:8 into refolding buffer. After treatment with endoproteinase over night at ambient temperature, equal amounts of control and test solutions were loaded onto a DEAE Sepharose column. The column was washed and the active enzyme was subsequently eluted with 60 mM Sodium Chloride in 20 mM Tris buffer pH 8.

TABLE 5

| | | Treatment | |
|---|---|---|---|
| Process Step | Parameter | Control | 0.11% CPC |
| Dissolution in 8 M Urea Post Clarification | Total $A_{280}$ | 960 | 494 |
| | Protein Content (mg)* | 490 | 272 |
| | pH | 9.5 | 9.5 |
| | Enzyme Activity (Units) | Inactive () | Inactive () |
| Post Chromatography of 26.5 mg of Refoldate (DEAE MP) | Protein Content (mg)* | 5.67 | 8.41 |
| | Enzyme Activity (Units) | 258 | 4043 |
| | Specific Activity (Units/mg) | 98 | 481 |

*Protein determination was carried out by the Bradford method.
(**) Prior to refolding the protein was inactive The results presented in Table 5 show that total OD in the CPC treated material dropped by 49.5% and the total protein content was reduced by 44.5%. Interestingly, total enzyme activity recovered in the CPC treated sample increased by 79%, suggesting that CPC removed a component that partially inhibited generation of active enzyme.

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

We claim:

1. A method for purifying a uricase comprising:
   a. obtaining a solution comprising a mixture of a solubilized uricase, one or more solubilized contaminating proteins and an alkaline buffer, wherein the uricase is positively charged under alkaline pH and has an isoelectric point greater than 7 and the one or more contaminating proteins has a polyanion charge;
   b. contacting the solution comprising the mixture of the solubilized uricase and the one or more solubilized contaminating proteins with one or more cationic surfactants in an amount effective to preferentially precipitate the one or more contaminating proteins, thereby increasing the proportion of proteins remaining in solution represented by the uricase; and
   c. recovering the uricase in solution after the preferential precipitation of step b;
   wherein the method is performed in the absence of a solid support and wherein the one or more cationic surfactants is an amphipathic ammonium compound selected from the group consisting of a quaternary ammonium compound of the general formula QN+; a paraffin chain primary ammonium compound of the general formula RNH3+; and a salt thereof.

2. The method of claim 1, wherein the amphipathic ammonium compound is selected from the group consisting of a cetylpyridinium salt, a stearamide-methylpyridinium salt, a lauryl pyridinium salt, a cetylquinolynium salt, a lauryl aminopropionic acid methyl ester salt, a lauryl amino propionic acid metal salt, a lauryl dimethyl betaine, a stearyl dimethyl betaine, a lauryl dihydroxyethyl betaine and a benzethonium salt.

3. The method of claim 2, wherein the amphipathic ammonium compound is selected from the group consisting of hexadecylpyridinium chloride, dequalinium acetate, cetyltrimethylammonium chloride, mixed n-alkyl dimethyl benzylammonium chloride, cetylpyridinium chloride, N,N-dimethyl-N-[2-[2-[4-(1,1,3,3,-tetramethylbutyl)-phenoxy]ethoxy]ethyl]benzenemethanammonium chloride, alkyl-dimethylbenzyl-ammonium chloride, dichloro-benzyldimethyl-alkylammonium chloride, tetradecyl trimethylammonium bromide, dodecyl trimethylammonium bromide, cetyltrimethylammonium bromide, lauryl dimethyl betaine stearyl dimethyl betaine, and lauryl dihydroxyethyl betaine.

4. The method of claim 2, wherein the amphipathic ammonium compound is a cetylpyridinium salt.

5. The method of claim 1, wherein the uricase is a recombinant protein.

6. The method of claim 1, wherein the one or more cationic surfactants are added to a concentration of from 0.001% to 5.0%.

7. The method of claim 6, wherein the one or more cationic surfactants are added to a concentration of from 0.01% to 0.5%.

8. The method of claim 6, wherein the one or more cationic surfactants are added to a concentration of from 0.03% to 0.2%.

9. The method of claim 1, wherein the method does not depend upon the presence of polyanions, solid supports and aggregates of the contaminating proteins.

10. The method of claim 9, wherein the one or more cationic surfactants are a cetylpyridinium salt.

11. The method of claim 10, wherein the cetylpyridinium salt is cetylpyridinium chloride.

12. The method of claim 1, wherein the solution has a pH that is about the same as the isoelectric point of the uricase.

13. The method of claim 1, wherein the solution has a pH that is below the isoelectric point of the uricase.

14. The method of claim 1, wherein the solution has a pH that is above the isoelectric point of the target protein and within 2 pH units of the isoelectric point of the target protein.

15. The method of claim 14, wherein the pH of the solution is within 1 pH unit of the isoelectric point of the target protein.

16. The method of claim 1, wherein the solution has a pH that is between 7 and 11.

17. The method of claim 1, wherein the solution has a pH that is between 8 and 11.

18. The method of claim 1, further comprising:
dissolving, in the presence of an alkaline buffer, one or more inclusion bodies from a bacterial cell that expresses the uricase, thereby providing the solubilized uricase and the one or more solubilized contaminating proteins of step a.

19. A method for purifying a uricase, comprising:
a. dissolving, in the presence of an alkaline buffer, one or more inclusion bodies from a bacterial cell that expresses the uricase, thereby providing a solubilized uricase and one or more solubilized contaminating proteins;
b. obtaining a solution comprising the solubilized uricase, the one or more solubilized contaminating proteins and the alkaline buffer;
c. contacting the solution comprising the solubilized uricase, the one or more solubilized contaminating proteins and the alkaline buffer with one or more cationic surfactants in an amount effective to preferentially precipitate the one or more contaminating proteins, thereby increasing the proportion of proteins remaining in solution represented by the uricase; and
d. recovering the uricase in solution after the preferential precipitation of step c:
e. wherein:
  (i) the method is performed in the absence of a solid support; or
  (ii) the one or more cationic surfactants are added to a concentration of from 0.03% to 0.2%; or
  (iii) both (i) and (ii); and
e. wherein the one or more cationic surfactants is an amphipathic ammonium compound selected from the group consisting of a cetylpyridinium salt, a stearamide-methylpyridinium salt, a lauryl pyridinium salt, a cetylquinolynium salt, a lauryl aminopropionic acid methyl ester salt, a lauryl amino propionic acid metal salt, a lauryl dimethyl betaine, a stearyl dimethyl betaine, a lauryl dihydroxyethyl betaine and a benzethonium salt.

20. The method of claim 19, wherein the one or more cationic surfactants are added to a concentration of from 0.03% to 0.1%.

21. The method of claim 19, wherein the amphipathic ammonium compound is a cetylpyridinium salt.

22. The method of claim 21, wherein the cetylpyridinium salt is cetylpyridinium chloride.

23. A method for purifying a target protein comprising:
a. obtaining a solution of a plurality of proteins, wherein the proteins in solution comprise the target protein, one or more contaminating proteins and an alkaline buffer, wherein the target protein is positively charged under alkaline pH and has an isoelectric point greater than 7 and the one or more contaminating proteins has a polyanion charge;
b. contacting the solution with one or more cationic surfactants in an amount effective to preferentially precipitate the one or more contaminating proteins, thereby increasing the proportion of proteins remaining in solution represented by the target protein; and
c. recovering the target protein in solution after the preferential precipitation of step b;
wherein the method is performed in the absence of a solid support;
wherein the one or more cationic surfactants are added to a concentration of from 0.03% to 0.2%;
wherein the target protein is selected from the group consisting of an antibody, a uricase, a factor X inhibitor, an acid deoxyribonuclease II, an elastase, a lysozyme, a papain, a peroxidase, a pancreatic ribonuclease, a trypsinogen, a trypsin, a cytochrome c, an erabutoxin, *staphylococcus aureus* enterotoxin C1, an interferon and a monoamine oxidase A; and wherein the one or more cationic surfactants is an amphipathic ammonium compound selected from the group consisting of a quaternary ammonium compound of the general formula QN+; a paraffin chain primary ammonium compound of the general formula RNH3+; and a salt thereof.

24. The method of claim 23, wherein the one or more cationic surfactants are added to a concentration of from 0.03% to 0.1%.

25. The method of claim 23, wherein the amphipathic ammonium compound is a cetylpyridinium salt.

26. The method of claim 25, wherein the cetylpyridinium salt is cetylpyridinium chloride.

27. The method of claim 23, wherein the target protein is a uricase.

28. The method of claim 23, wherein the amphipathic ammonium compound is selected from the group consisting of a cetylpyridinium salt, a stearamide-methylpyridinium salt, a lauryl pyridinium salt, a cetylquinolynium salt, a lauryl aminopropionic acid methyl ester salt, a lauryl amino propionic acid metal salt, a lauryl dimethyl betaine, a stearyl dimethyl betaine, a lauryl dihydroxyethyl betaine and a benzethonium salt.

29. The method of claim 28, wherein the amphipathic ammonium compound is selected from hexadecylpyridinium chloride, dequalinium acetate, cetyltrimethylammonium chloride, mixed n-alkyl dimethyl benzylammonium chloride, cetylpyridinium chloride, N,N-dimethyl-N-[2-[2-[4-(1,1,3,3,-tetramethylbutyl)-phenoxy]ethoxy]ethyl]benzenemethanammonium chloride, alkyl-dimethylbenzyl-ammonium chloride, dichloro-benzyldimethyl-alkylammonium chloride, tetradecyl trimethylammonium bromide, dodecyl trimethylammonium bromide, cetyltrimethylammonium bromide, lauryl dimethyl betaine stearyl dimethyl betaine, and lauryl dihydroxyethyl betaine.

30. The method of claim 23, further comprising:
dissolving one or more inclusion bodies from a bacterial cell that expresses the target protein, thereby providing the target protein, and the one or more contaminating proteins, in solution, of step a.

* * * * *